(12) United States Patent
Fang et al.

(10) Patent No.: US 11,744,711 B2
(45) Date of Patent: Sep. 5, 2023

(54) SPINAL INTERBODY DEVICES WITH DENSITY GRADIENTS AND ASSOCIATED METHODS

(71) Applicant: Orthofix US LLC, Lewisville, TX (US)

(72) Inventors: Samuel Fang, Plano, TX (US); Easton Braithwaite, Anna, TX (US); Brian Dewillie, Addison, TX (US)

(73) Assignee: Orthofix US LLC, Lewisville, TX (US)

( * ) Notice: Subject to any disclaimer, the term of this patent is extended or adjusted under 35 U.S.C. 154(b) by 263 days.

(21) Appl. No.: 17/208,546

(22) Filed: Mar. 22, 2021

(65) Prior Publication Data

US 2022/0296386 A1 Sep. 22, 2022

(51) Int. Cl.
*A61F 2/44* (2006.01)
*A61F 2/30* (2006.01)

(52) U.S. Cl.
CPC ........ *A61F 2/4455* (2013.01); *A61F 2/30771* (2013.01); *A61F 2002/30006* (2013.01); *A61F 2002/3008* (2013.01); *A61F 2002/3092* (2013.01); *A61F 2002/30784* (2013.01); *A61F 2310/00023* (2013.01)

(58) Field of Classification Search
CPC .......... A61F 2/44; A61F 2/442; A61F 2/4455; A61F 2/446; A61F 2/4465; A61F 2/447; A61F 2002/30006; A61F 2002/30056; A61F 2002/3008; A61F 2002/3092; A61F 2310/00023
See application file for complete search history.

(56) References Cited

U.S. PATENT DOCUMENTS

| | | | |
|---|---|---|---|
| 7,208,222 B2 | 4/2007 | Rolfe et al. |
| 7,241,313 B2 | 7/2007 | Unwin et al. |
| 7,393,559 B2 | 7/2008 | Groza et al. |
| 7,951,412 B2 | 5/2011 | Justin et al. |
| 9,610,174 B2 | 4/2017 | Wang et al. |
| 10,420,597 B2 | 9/2019 | Papangelou et al. |

(Continued)

FOREIGN PATENT DOCUMENTS

| | | |
|---|---|---|
| CN | 110179570 A | 8/2019 |
| WO | 2009120886 A2 | 10/2009 |
| WO | 2017134424 A1 | 8/2017 |

OTHER PUBLICATIONS

US 9,642,715, May 9, 2017, Kelly et al. (withdrawn).

(Continued)

*Primary Examiner* — Eric S Gibson
(74) *Attorney, Agent, or Firm* — HAYNES AND BOONE, LLP

(57) ABSTRACT

An interbody device configured for insertion between adjacent vertebrae includes a body comprising and exterior surface and an interior surface defining a cavity. The body comprises a visualization window extending between the exterior surface and the interior surface, where the visualization window comprises a lattice of radiopaque structures. A density of the lattice in a central region of the visualization window is less than in the density of the lattice in an outer region of the visualization window such that the visualization window is radiolucent through the central region.

20 Claims, 18 Drawing Sheets

(56) References Cited

U.S. PATENT DOCUMENTS

| | | | |
|---|---|---|---|
| 10,660,764 B2 | 5/2020 | Maglaras et al. | |
| 10,675,158 B2 | 6/2020 | Unger et al. | |
| 10,772,732 B1* | 9/2020 | Miller | A61F 2/30771 |
| 11,179,247 B2* | 11/2021 | Jebsen | A61F 2/447 |
| 11,278,427 B2* | 3/2022 | Picha | A61F 2/442 |
| 11,446,159 B2* | 9/2022 | Mirda | A61F 2/4611 |
| 2003/0074081 A1 | 4/2003 | Ayers | |
| 2010/0137990 A1 | 6/2010 | Apatsidis et al. | |
| 2013/0116793 A1* | 5/2013 | Kloss | A61F 2/442 |
| | | | 623/17.16 |
| 2013/0325129 A1* | 12/2013 | Huang | A61F 2/44 |
| | | | 623/17.16 |
| 2014/0236229 A1 | 8/2014 | Longo et al. | |
| 2017/0333205 A1* | 11/2017 | Joly | A61F 2/30771 |
| 2018/0110624 A1* | 4/2018 | Arnone | A61F 2/30767 |
| 2018/0256336 A1* | 9/2018 | Mueller | A61F 2/2846 |
| 2018/0303624 A1* | 10/2018 | Shoshtaev | A61F 2/4465 |
| 2018/0333272 A1* | 11/2018 | Mirda | A61F 2/30771 |
| 2019/0091027 A1* | 3/2019 | Asaad | A61F 2/447 |
| 2019/0314169 A1 | 10/2019 | Patel et al. | |
| 2020/0093612 A1* | 3/2020 | Blain | A61F 2/447 |
| 2020/0188130 A1* | 6/2020 | Jebsen | A61F 2/447 |
| 2020/0197565 A1* | 6/2020 | Suh | A61F 2/447 |
| 2020/0289288 A1* | 9/2020 | Muller | B33Y 80/00 |
| 2020/0297505 A1* | 9/2020 | McLaughlin | A61F 2/4455 |
| 2021/0038403 A1* | 2/2021 | Neary | A61F 2/447 |
| 2021/0085481 A1* | 3/2021 | Cain | A61F 2/4455 |
| 2021/0154023 A1* | 5/2021 | Picha | A61F 2/442 |
| 2022/0296386 A1* | 9/2022 | Fang | B33Y 80/00 |

OTHER PUBLICATIONS

International Search Report and Written Opinion received in Patent Cooperation Treaty Application No. PCT/US2022/020363, dated Jun. 2, 2022, 8 pages.

Global Cascadia Lateral 3D Sell Sheet SMACC Approved (2 pgs).

TMArdis Interbody System Brochure (4 pgs).

* cited by examiner

SPINAL INTERBODY DEVICES WITH DENSITY GRADIENTS AND ASSOCIATED METHODS

TECHNICAL FIELD

The present disclosure relates generally to a composite interbody device adapted for insertion between two adjacent vertebrae to promote the fusion of two vertebrae.

BACKGROUND

The bones and connective tissue of an adult human spinal column consists of more than 20 discrete bones coupled sequentially to one another by a tri-joint complex. The complex consists of an anterior disc and two posterior facet joints. The anterior discs of adjacent bones are cushioned by cartilage spacers referred to as intervertebral discs. The over 20 bones of the spinal column are anatomically categorized as one of four classifications: cervical, thoracic, lumbar, or sacral. The cervical portion of the spine which comprises the top of the spine up to the base of the skull, includes the first 7 vertebrae. The intermediate 12 bones are thoracic vertebrae, and connect to the lower spine comprising the 5 lumbar vertebrae. The base of the spine are sacral bones, including the coccyx.

The spinal column of bones is highly complex in that it includes over 20 bones coupled to one another, housing and protecting critical elements of the nervous system having innumerable peripheral nerves and circulatory bodies in close proximity Despite its complexity, the spine is a highly flexible structure, capable of a high degree of curvature and twist in nearly every direction.

Genetic or developmental irregularities, trauma, chronic stress, tumors and disease, however, can result in spinal pathologies which either limit this range of motion or threaten the critical elements of the nervous system housed within the spinal column. A variety of systems have been disclosed in the art which achieve immobilization by implanting artificial assemblies in or on the spinal column. These assemblies may be classified as anterior, posterior or lateral implants. Lateral and anterior assemblies are coupled to the anterior portion of the spine which is in the sequence of vertebral bodies. Posterior implants generally comprise pairs of rods ("bilateral spinal support rods"), which are aligned along the axis which the bones are to be disposed, and which are then attached to the spinal column by either hooks which couple to the lamina or attach to the transverse processes, or by screws which are inserted through pedicles.

Spinal fusion treatment is commonly used to treat spinal disc disease and/or spinal instability. The degeneration of spinal discs can create significant pain and discomfort for individuals suffering from this affliction. In many cases, this pain can be alleviated by immobilizing the vertebrae adjacent to the degenerated disc and encouraging bone growth across the immobilized area of the spine. Conventional spinal implants are designed to facilitate bone through-growth, or fusion resulting from growth of bone through holes or channels through the implants. Although effective, the bone through-growth process is slow, sometimes taking more than a year to complete. Through-growth can be further delayed if the implant area is not immobilized. Even micro-motion of the implant area can disturb and disrupt bone growth, leading to increased incidence of subsidence and pseudarthrosis.

Some conventional devices attempt to improve implant stabilization by encouraging bone on-growth—a comparatively rapid, planar growth of bone upon surfaces of an adjacent implant, or upon surfaces of adjacent bone. For example, on-growth may be encouraged by coating a titanium cage with a chemical such as hydroxyapatite to encourage new-grown bone to adhere to the implant surface. However, because titanium is radiopaque, titanium implants can interfere with diagnostic assessment of bone growth, whether coated with hydroxyapatite or not. For example, titanium implants may obscure visualization of bone growth (e.g., through-growth) on x-rays, making it difficult to determine if fusion has occurred.

SUMMARY

Various embodiments of an interbody device for use with spinal fusion surgery are described herein. The interbody device may include body having apertured or porous visualization windows, and solid scaffold portions. The visualization windows may have a porosity gradient or density gradient along at least one axis of the implant. In some embodiments, the density decreases toward the center of the visualization windows to provide for increased radiotransparency. The visualization windows may have higher densities near the outer edges and outer areas of the visualization windows to maintain strength and structural integrity under the load of the spine. The density may vary as a gradient, which may be linear or nonlinear. The solid scaffold portions provide additional strength and reinforcement. Accordingly, the implants provided herein are sufficiently strong for use as interbody devices in spinal fusion surgery, while allowing for x-ray imaging through the visualization windows for monitoring the progress of bone in-growth into the porous structures of the implants.

According to one embodiment, an interbody device configured for insertion between adjacent vertebrae includes a body comprising and exterior surface and an interior surface defining a cavity. The body comprises a visualization window extending between the exterior surface and the interior surface, where the visualization window comprises a lattice of radiopaque structures. A density of the lattice in a central region of the visualization window is less than in the density of the lattice in an outer region of the visualization window such that the visualization window is radiolucent through the central region.

In some aspects, the body comprises a top side and a bottom side, and wherein the lattice comprises a first density gradient along a first direction extending between the top side and the bottom side. In some aspects, the lattice comprises a second density gradient along a second direction transverse to the first direction. In some aspects, the first density gradient linearly decreases from the outer region of the visualization window to the central region of the visualization window. In some aspects, the density of the lattice of the outer region of the visualization window is associated with a porosity of 40%-60%, and wherein the density of the lattice of the central region of the visualization window is associated with a porosity of 70%-90%.

In some aspects, the visualization window comprises a first constant density region in the outer region. In some aspects, the first constant density region extends from a bottom edge of the body to a first intermediate region between the bottom edge and the central region of the visualization window. In some aspects, the lattice of radiopaque structures comprises a gyroid architecture. In some aspects, the density of the lattice is based on geometric parameters of the gyroid architecture.

In some aspects, the body comprises a plurality of solid scaffold regions, wherein the visualization window is disposed between two solid scaffold regions. In some aspects, the body comprises a sidewall extending from the exterior surface to the interior surface, and wherein the plurality of solid scaffold regions occupy only a portion of a thickness of the sidewall. In some aspects, the device further includes a solid wall on a lateral side of the bod. In some aspects, the body defines one or more passages extending through the solid wall on the lateral side of the body. In some aspects, the body comprises a sidewall extending from the exterior surface to the interior surface, and wherein the lattice of the visualization window occupies an entire thickness of the sidewall. In some embodiments, the lattice of radiopaque structures comprises a metal. In some embodiments, the lattice of radiopaque structures comprises titanium.

According to another embodiment of the present disclosure, an intervertebral spacer configured to be placed between two adjacent vertebrae includes: a solid portion comprising a plurality of solid scaffold regions, wherein the solid scaffold regions are disposed around an opening; and a visualization window disposed between two or more of the solid scaffold regions and around the opening. The visualization window comprises a lattice of radiopaque surfaces defining a network of pores. A density of the lattice is greater in an outer region of the visualization window than in a central region of the visualization window such that the visualization window is radiolucent in the central region.

In some aspects, the solid portion and the visualization window form a unitary body. In some embodiments, the lattice varies linearly in density from the outer region to a center of the central region along a vertical axis. In some embodiments, the visualization window further comprises a constant density region positioned above the outer region such that the outer region is disposed between the constant density region and the central region. In some aspects, the density of the lattice is constant in the constant density region along a vertical axis. In some embodiments, the network of pores extends from an exterior surface to the opening.

Additional aspects, features, and advantages of the present disclosure will become apparent from the following detailed description.

BRIEF DESCRIPTION OF THE DRAWINGS

For a more complete understanding of the present disclosure and its advantages, reference is now made to the following description taken in conjunction with the accompanying drawings, in which like reference numbers indicate like features, and.

Although similar reference numbers may be used to refer to similar elements for convenience, it can be appreciated that each of the various example embodiments may be considered to be distinct variations.

DETAILED DESCRIPTION

Exemplary embodiments will now be described hereinafter with reference to the accompanying figures, which form a part hereof, and which illustrate examples by which the exemplary embodiments, and equivalents thereof, may be practiced. As used in the disclosures and the appended claims, the terms "embodiment," "example embodiment" and "exemplary embodiment" do not necessarily refer to a single embodiment, although it may, and various example embodiments, and equivalents thereof, may be readily combined and interchanged, without departing from the scope or spirit of present embodiments. Furthermore, the terminology as used herein is for the purpose of describing example embodiments only and is not intended to be limitations of the embodiments. In this respect, as used herein, the term "plate" may refer to any substantially flat structure or any other three-dimensional structure, and equivalents thereof, including those structures having one or more portions that are not substantially flat along one or more axis. Furthermore, as used herein, the terms "opening," "recess," "aperture," and equivalents thereof, may include any hole, space, area, indentation, channel, slot, bore, and equivalents thereof, that is substantially round, oval, square, rectangular, hexagonal, and/or of any other shape, and/or combinations thereof, and may be defined by a partial, substantial or complete surrounding of a material surface. Furthermore, as used herein, the term "in" may include "in" and "on," and the terms "a," "an" and "the" may include singular and plural references. Furthermore, as used herein, the term "by" may also mean "from," depending on the context. Furthermore, as used herein, the term "if" may also mean "when" or "upon," depending on the context. Furthermore, as used herein, the words "and/or" may refer to and encompass any and all possible combinations of one or more of the associated listed items.

Figure 1A:
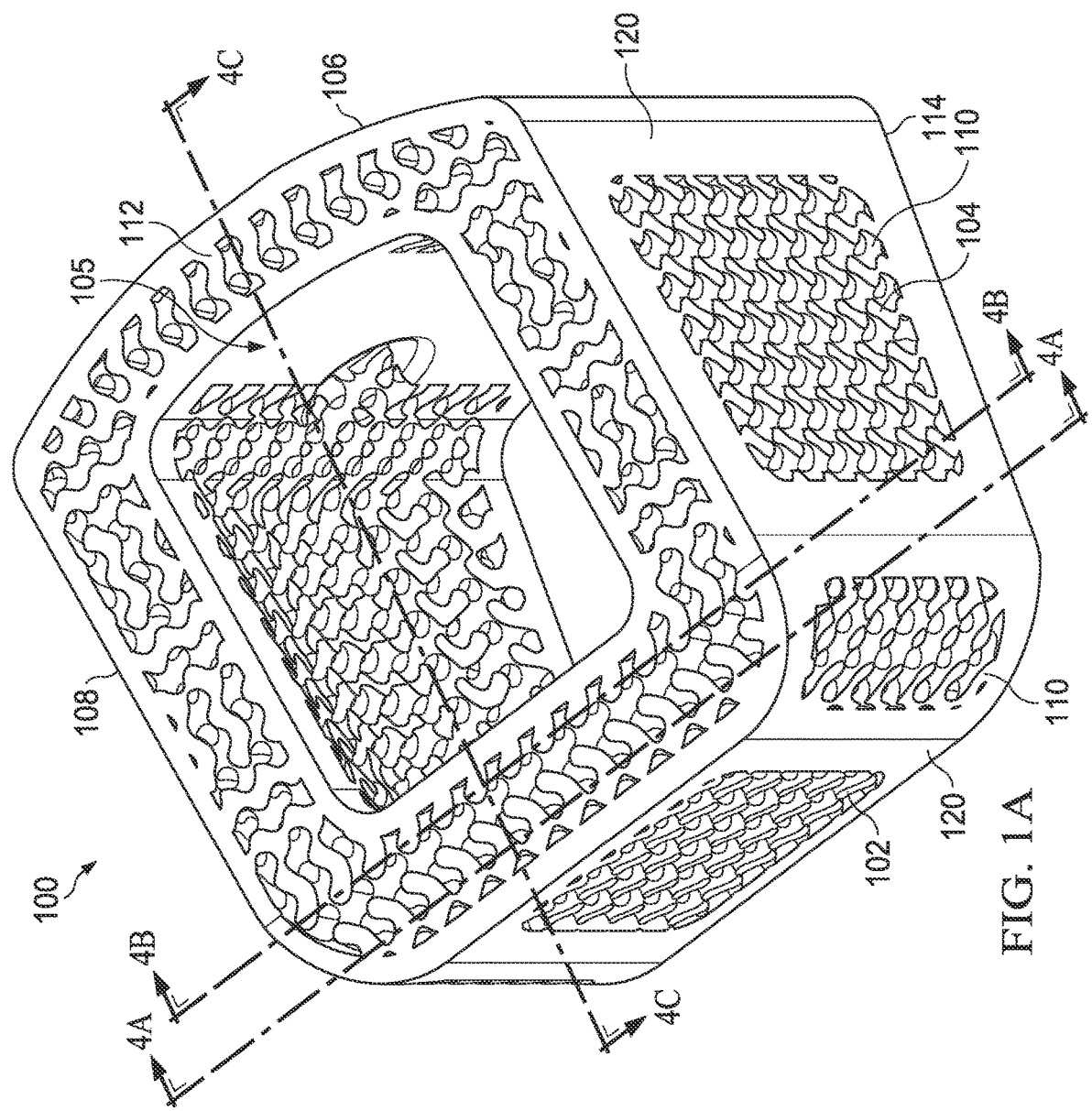
FIG. 1A is a perspective view of an interbody implant having a plurality of visualization windows according to aspects of the present disclosure.
Figure 1B:
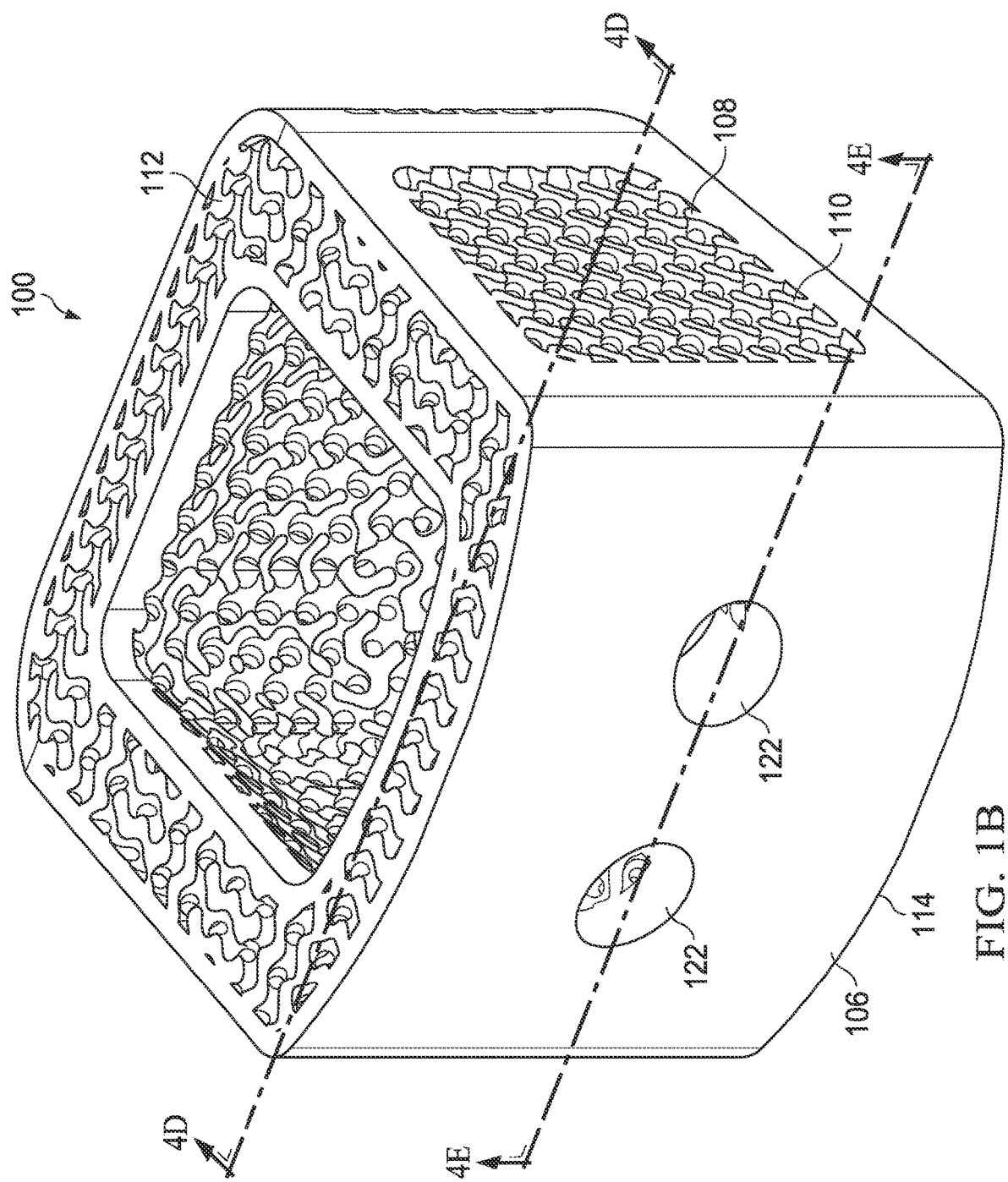
FIG. 1B is a perspective view of an interbody implant having a plurality of visualization windows according to aspects of the present disclosure.

FIGS. 1A and 1B are perspective views of an interbody implant device 100. The implant device 100 is sized, shaped, and structurally configured to be positioned between adjacent vertebrae in a human spine. In particular, the implant device 100 is configured to be positioned between cervical vertebrae. The implant 100 has a body including a plurality of lateral sides or faces defining and surrounding a cavity 105. In particular, the implant 100 includes a front side 102, a lateral side 104, a rear side 106, and a lateral side 108. The implant 100 also includes a top surface 112 and a bottom surface 114, each arranged around the cavity 105, which may also be referred to as an opening. The implant 100 includes apertured portions and solid portions, which will be described further below with respect to FIG. 2. In some aspects, the apertured portions may be referred to as porous portions, where the pores include a network of holes or passages in the body of the implant 100. The apertured portions may also be referred to as cavernous portions, cavitated portions, for example. The apertured portions comprise a plurality of visualization windows 110 including one or more apertures or pores extending into and/or through a thickness of each side (e.g., 102, 104) of the implant 100. The implant 100 includes visualization windows 110 on the front side 102, the lateral side 104, and the lateral side 108. The implant 100 also includes solid scaffolding portions or regions 120, which do not include the apertures present in the visualization windows 110. In the illustrated embodiment, the solid scaffolding portions 120 and the visualization windows 110 form a singular or integral structure. For example, the implant 100 may be manufactured using an additive manufacturing process, such as a three-dimensional (3D) printing process or metal sintering process in which the solid scaffold portions 120 and the visualization windows 110 are formed together in a layered process. In other embodiments, the solid scaffold portions 120 and the visualization windows 110 comprise separate components joined together during manufacturing.

In other embodiments, the implant 100 may comprise separate components coupled or otherwise joined together during a manufacturing process. For example, the implant 100 may include a unitary frame structure similar to the scaffold portions 120, and the lattice structure, including the visualization windows 110, may be inserted and joined to the frame structure during assembly. In some embodiments, the lattice structure and/or visualization windows 110 comprise a different material than the scaffold portions 120. For example, in some embodiments, the scaffold portions 120 include a metallic material (e.g., titanium) and the visualization windows 110 include a polymer (e.g., polyether ether ketone (PEEK)). In other embodiments, the visualization windows 110 are formed of a same type of material.

Referring to FIG. 1B, the rear side 106 of the implant 100 includes a solid surface, which may be referred to as non-porous or non-apertured. However, it will be understood that "porous" refers to the apertures or passageways present in the visualization windows 110. The non-porous surface of the rear side 106 may include micropores or nanopores in the surface, which may manifest as a relatively rough surface to a human observer. The implant 100 includes two positioning holes 122 extending through the rear side 106 and in communication with the cavity 105. As will be explained further below, the positioning holes 122 may be configured to receive a positioning tool (see 550, FIG. 9) for placement of the implant 100 between the vertebrae of the patient's spine.

The visualization windows 110 include a network or pores or apertures extending through a thickness of the lateral sides of the implant 100. Thus, the density of the implant 100 in the regions of the visualization windows 110 is lower than the density of the implant 100 in the solid scaffold regions 120. Stated differently, the porosity of the implant 100 in the regions of the visualization windows 110 is higher than the porosity of the implant 100 in the solid scaffold regions 120. In this regard, the density of the implant 100, which has a porous structure, may be inversely related to the porosity of the implant 100. The porosity of the implant may be described as the ratio of porous volume to solid volume. The lower density of the visualization windows 110 may facilitated bone in-growth for better incorporation and long-term stability of the implant 100 within the patient's spine. Further, the lower density of the visualization windows 110 provides for improved visualization of bone in-growth within the cavity 105 of the implant 100. In one aspect of the present disclosure, the density or porosity of the implant 100 in the visualization windows 110 may vary to provide for enhanced radiological visibility while providing sufficient strength to support the load of the patient's body. In this regard, the density of the apertured visualization windows 110 defined by interconnected lattices may be relatively higher in a central region of the visualization windows 110 than in an outer region of the visualization windows 110. In an inverse relationship, the lattices forming the windows can be higher in an outer region than in a central region of the visualization window. For the purposes of the present disclosure, the porous or apertured visualization windows may be described as having porosity gradients, or density gradients. In this regard, because the porosity of the lattice structures, including the visualization windows 110, varies, the density also varies inversely to the porosity.

In the illustrated embodiment, the apertured portion of the implant 100 includes a gyroid architecture. The gyroid architecture includes a periodic minimal surface defining a network or labyrinth of interconnected passageways. The geometric parameters of the gyroid structure may be configured using one or more input parameters, which may adjust the size of the apertures (e.g., diameter), the spacing between apertures, or any other associated parameter. Accordingly, the density of each visualization window 110 may be configured by setting the geometric parameters of the gyroid structure. As will be explained further below, the density of each visualization window 110 may vary along one or more axes. For example, in some embodiments, the density of each visualization window 110 may increase along a vertical axis extending from the bottom surface 114 of the implant 100 to the top surface 112 of the implant 100 such that the density of the visualization window 110 reaches a minimum at the center of the visualization window, and reaches maxima at the upper and lower regions of the visualization window 110. In other words, the porosity of each visualization window 110 may reach a maximum at the center of the visualization window 110, and may reach minima at the upper and lower regions of the visualization window 110. In some aspects, the density of the visualization windows 110 varies as the size of the apertures or passageways of the apertured portion increases or decreases.

The apertures or passageways of the apertured portion of the implant 100 may be interconnected to provide for improved bone in-growth. Although the embodiment shown in FIGS. 1A and 1B has a gyroid architecture, it will be understood that other types of apertured bodies are contemplated by the present disclosure. For example, the implant 100 may include arrays of orthogonal apertures that intersect, or do not intersect. In particular, the implant 100 may include an apertured structure similar to that described in U.S. Pat. No. 9,693,874, issued Jul. 4, 2017, the entirety of which is hereby incorporated by reference. In other embodiments, the porous or apertured portion of the implant 100 may be formed by pressing or melting together small metal beads or particles of various sizes together to form the implant 100. The spaces or gaps between the metal particles may vary in size, such that the radiolucent see between the visualization windows 110 increases toward the center of each visualization.

The embodiment of the implant 100 shown in FIGS. 1A and 1B may be configured for use between the cervical vertebrae of the patient. However, as will be explained further below, the present application also contemplates interbody implants configured for use in other areas of the spine, such as between the lumbar vertebrae. The implant 100 may be metallic, in some embodiments. For example, the implant 100 may include titanium. In other embodiments, the implant 100 may be formed of a polymer material, such as polyether ether ketone (PEEK). The polymer material may be radiopaque. For example, the polymer may be impregnated with particles of a radiopaque material, such as Barium Sulfate, Bismuth, Tungsten, and/or any other suitable metal or radiopaque material. In some embodiments, one or more of the components are formed of bone or other naturally occurring material with sufficient strength for use as an spinal implant. In other embodiments, one or more components of the implant 100 may include a calcium-based substance.

Figure 2:
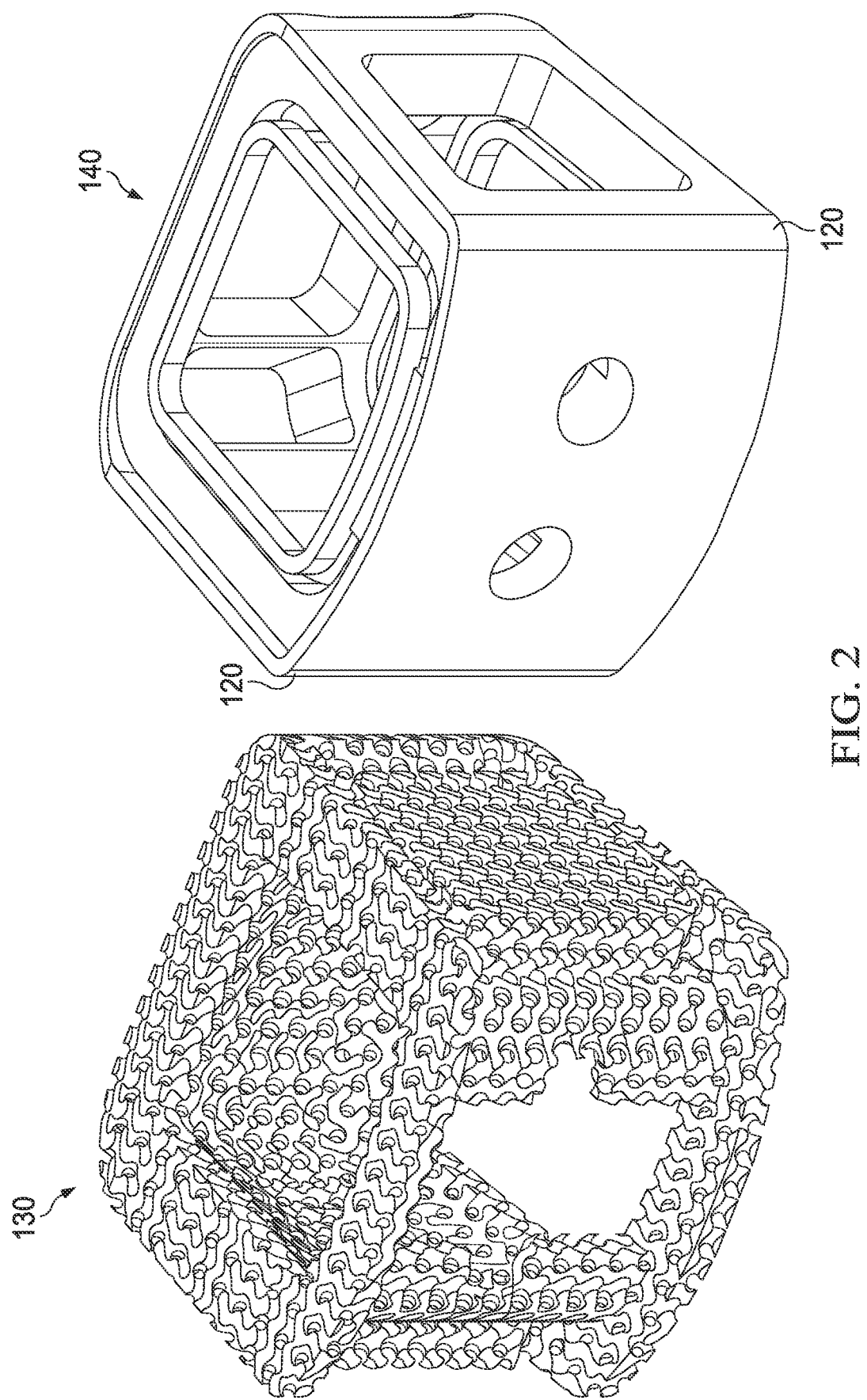
FIG. 2 is an exploded view of an interbody implant having a plurality of visualization windows according to aspects of the present disclosure.

FIG. 2 is an exploded view of the interbody implant 100 shown in FIGS. 1A and 1B. In particular, FIG. 2 shows an apertured portion 130 and a solid scaffolding portion 140. Although shown separately, it will be understood that the apertured portion 130 and the solid scaffolding portion 140 may form an integral single structure, as explained above with respect to FIGS. 1A and 1B. FIG. 2 illustrates, conceptually, the functional aspects of the apertured portion 130 and the solid scaffolding portion 140.

The apertured portion 130 varies in density or porosity along an axis extending from the bottom surface 114 and the top surface 112. The density reaches a minimum at or near the center of the body along the axis. The density decreases as the size of the apertures increases. In other words, the porosity may be described as increasing as the size of the apertures of passageways increases. Stated differently, the density decreases as the interstitial surfaces defining the apertures decrease in thickness. As the interstitial surfaces forming the gyroid structure increase in thickness for upper and lower regions of the apertured portion 130, the density increases in the porosity decreases. The internal pore size (e.g., diameter) of the passageways in the apertured portion 130 may vary from 150 μm to 700 μm. However, it will be understood that these values are merely exemplary and that the pore sizes or diameters may have other values both greater or smaller. Further, although the size of the passageways may be described in terms of diameter in some instances, the passageways may not have circular cross-sections. In this regard, the term "diameter" may describe the average distance from one side or boundary of a passageway to an opposing side or boundary of the passageway.

The solid scaffolding portion 140 includes a plurality of scaffolds 120. Some of the scaffolds 120 may extend vertically from the bottom surface 114 to top surface 112. Other scaffolds 120 extend horizontally at or near the top surface 112 and the bottom surface 114. Solid scaffolding portion 140 provides more strength and rigidity of the implant 100 to support the load of the spine. As shown in FIG. 2, the gyroid structural apertures are not present in the solid scaffolding portion 140. However, it will be understood that the solid scaffolding portion may include micropores or nano for formed by etching, sandblasting, or any other suitable process to provide a rough surface. The roughened surface of the solid scaffolding portion 140 may provide for increased adhesion to the bone and biological structures in the spine.

As will be explained further below, the apertured portion 130 may include one or more regions of constant density or porosity along the axis. The constant density portions may have a relatively higher density (or lower porosity) and may provide increased strength and rigidity of the apertured portion 130 around an exterior of the implant 100. Further, the gradient of the density of the apertured portion 130 may balance the strength of the implant 100 with the increased radiolucency or visibility through the visualization window 110. Accordingly, the implant 100 allows for visualization through visualization windows 110 while maintaining sufficient strength and rigidity to support the load of the spine.

Figure 3A:
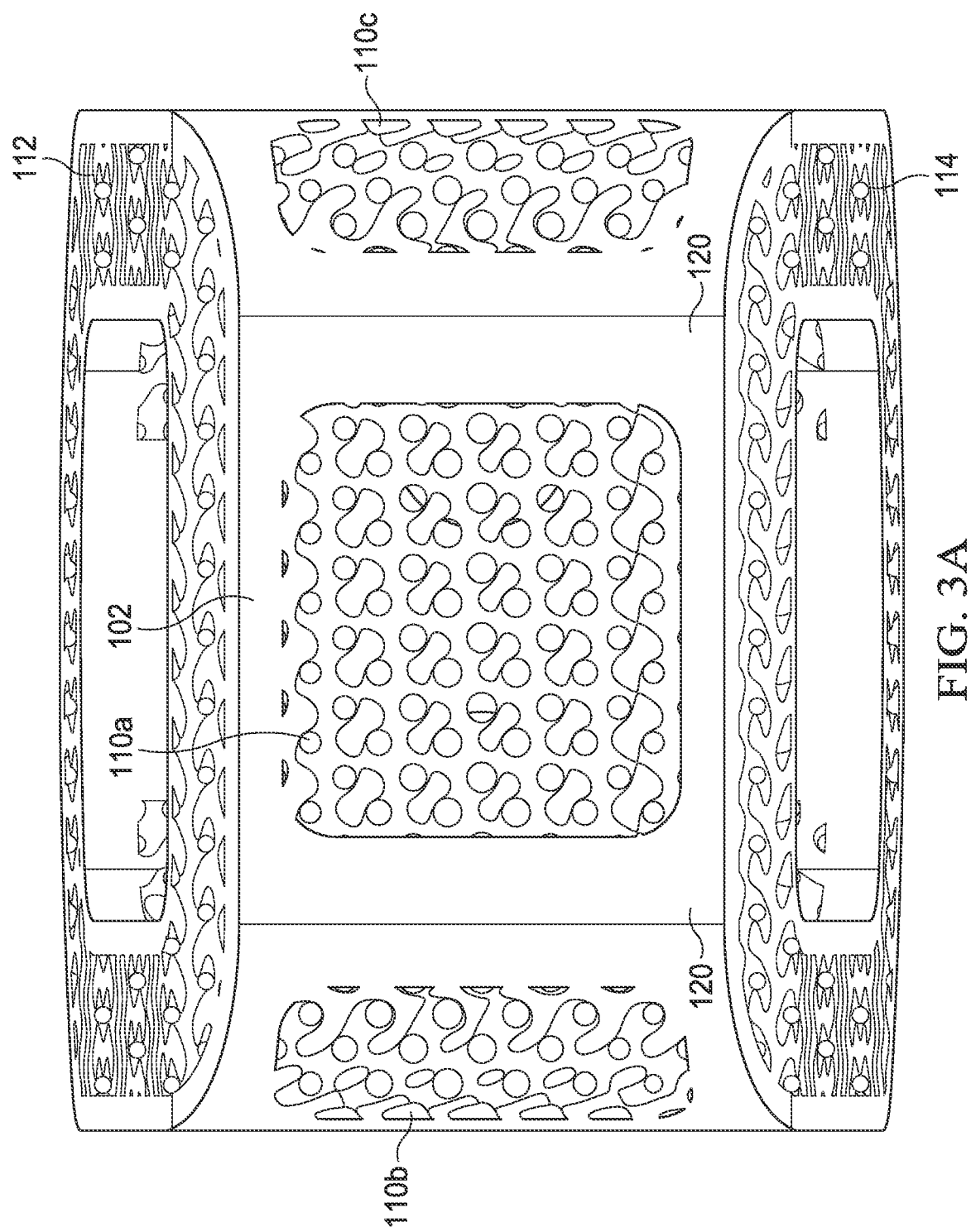
FIG. 3A is a front elevation view of the interbody implant of FIGS. 1A and 1B according to aspects of the present disclosure.
Figure 3B:
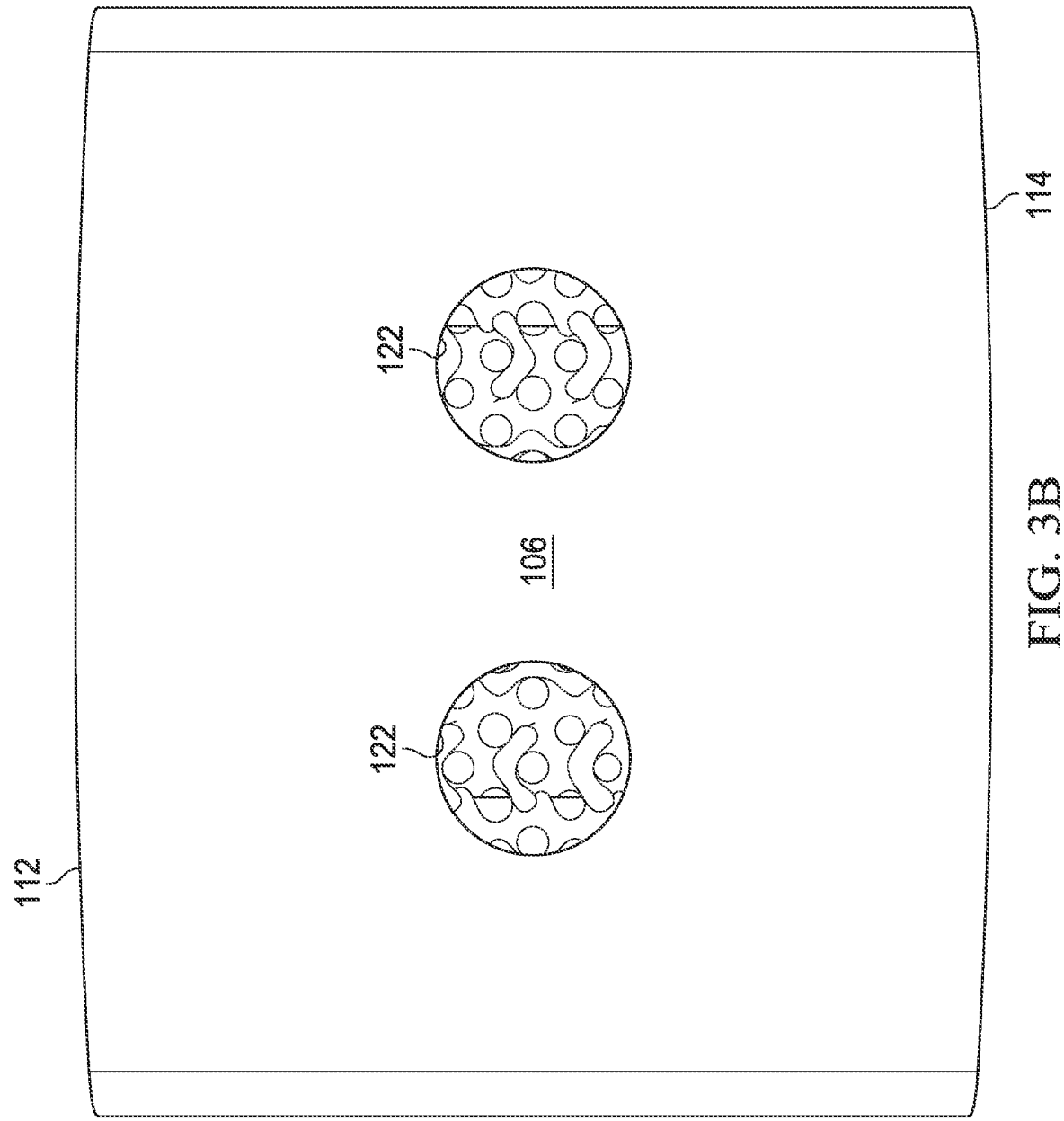
FIG. 3B is a rear elevation view of the interbody implant of FIGS. 1A and 1B according to aspects of the present disclosure.
Figure 3C:
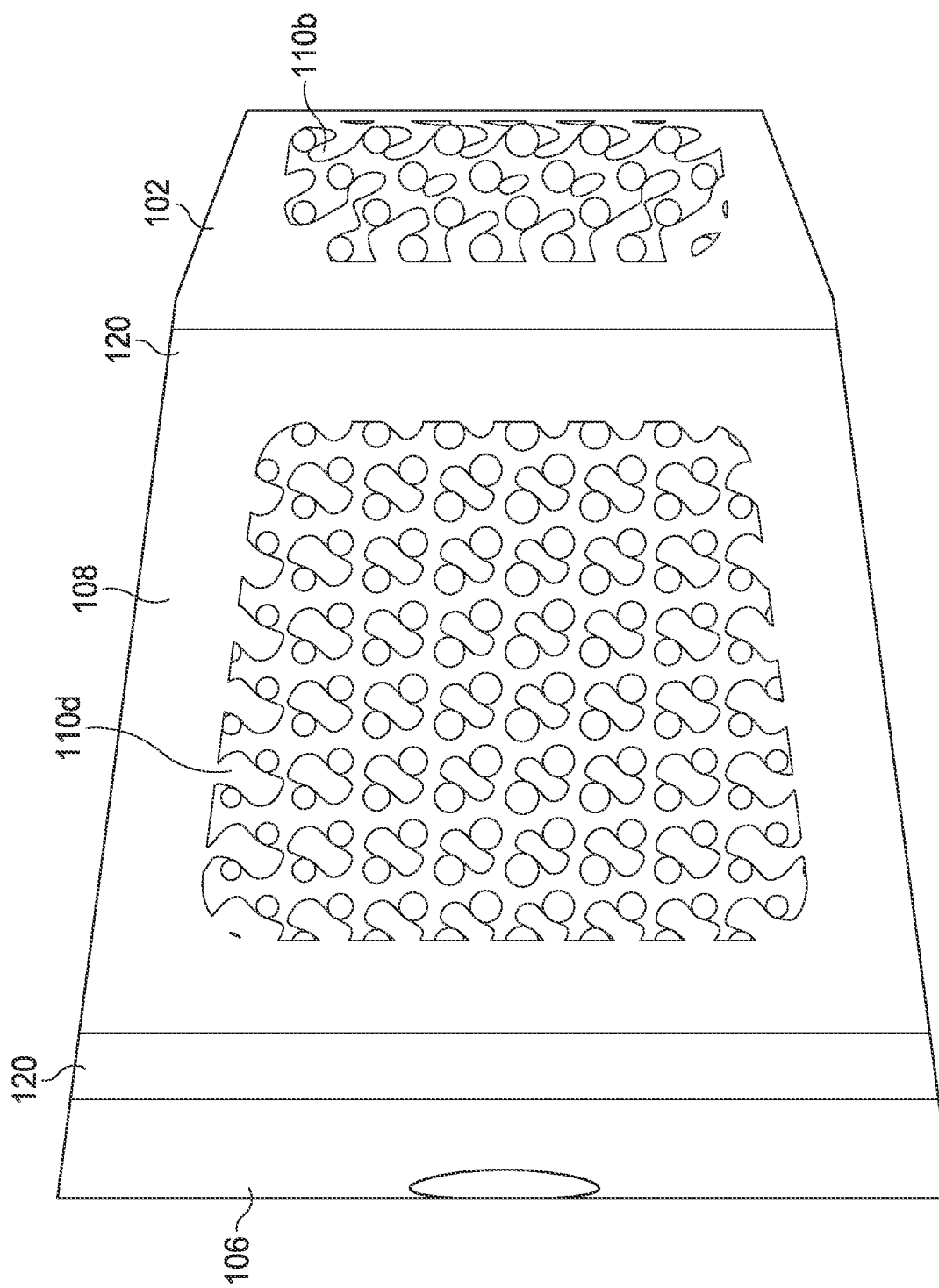
FIG. 3C is a side elevation view of the interbody implant of FIGS. 1A and 1B according to aspects of the present disclosure.

FIGS. 3A, 3B, and 3C are side elevation views of different sides or faces of the implant 100. FIG. 3A is a side elevation view of the front side 102, FIG. 3B is a side elevation view of the rear side 106 of the implant 100, and FIG. 3C is a side elevation view of the lateral side 108 of the implant 100. Referring to FIG. 3A, the implant 100 includes on the front side 102, a first visualization window 110a disposed on a central region of the front side 102 and corner visualization windows 110b and 110c on the outer edges or corners of the front side 102. The front side 102 also includes scaffold portion 120 between the first visualization window 110a and the corner visualization windows 110b, 110c. The scaffold portions 120 also extend horizontally along the bottom surface 114 and the top surface 112 of the implant 100. The porosity of all three visualization windows 110a, 110b, and 110c increases toward the center of each visualization window 110.

As shown in FIG. 3B, the rear side 106 of the implant 100 includes a solid surface and two positioning holes 122. The solid surface of the rear side 106 may extend through an entire thickness of the rear side 106. The solid portion of the rear side 106 may provide for increased strength for the positioning holes 122. The positioning holes 122 are configured to receive a positioning tool for placement of the implant 100 in between adjacent vertebrae of the patient's spine. In some aspects, a significant amount of force and impact may be applied to the implant 100 via the positioning holes 122. Accordingly, the solid portion of the rear side 106 provides increased strength against the force and impact during placement of the implant 100 patient's spine. In the illustrated embodiment, the rear side 102 may be largest side. The shape of the implant 100 and the proportionality of the front side one of to the rear side 106 lateral sides 104, 108 may be configured based on the curvature of the patient's spine (e.g., lordosis) at the location of the implant 100. In this regard, the lateral side 108 is shown as having a trapezoidal, or wedge shape. The wedge-shaped of the lateral side 108 (and the corresponding lateral side 14) may coincide with the curvature of the patient's spine. The lateral side 108 shown in FIG. 3C has a single visualization window 110d and solid scaffold portions 120 on each side of the visualization window 110d.

Figure 4A:
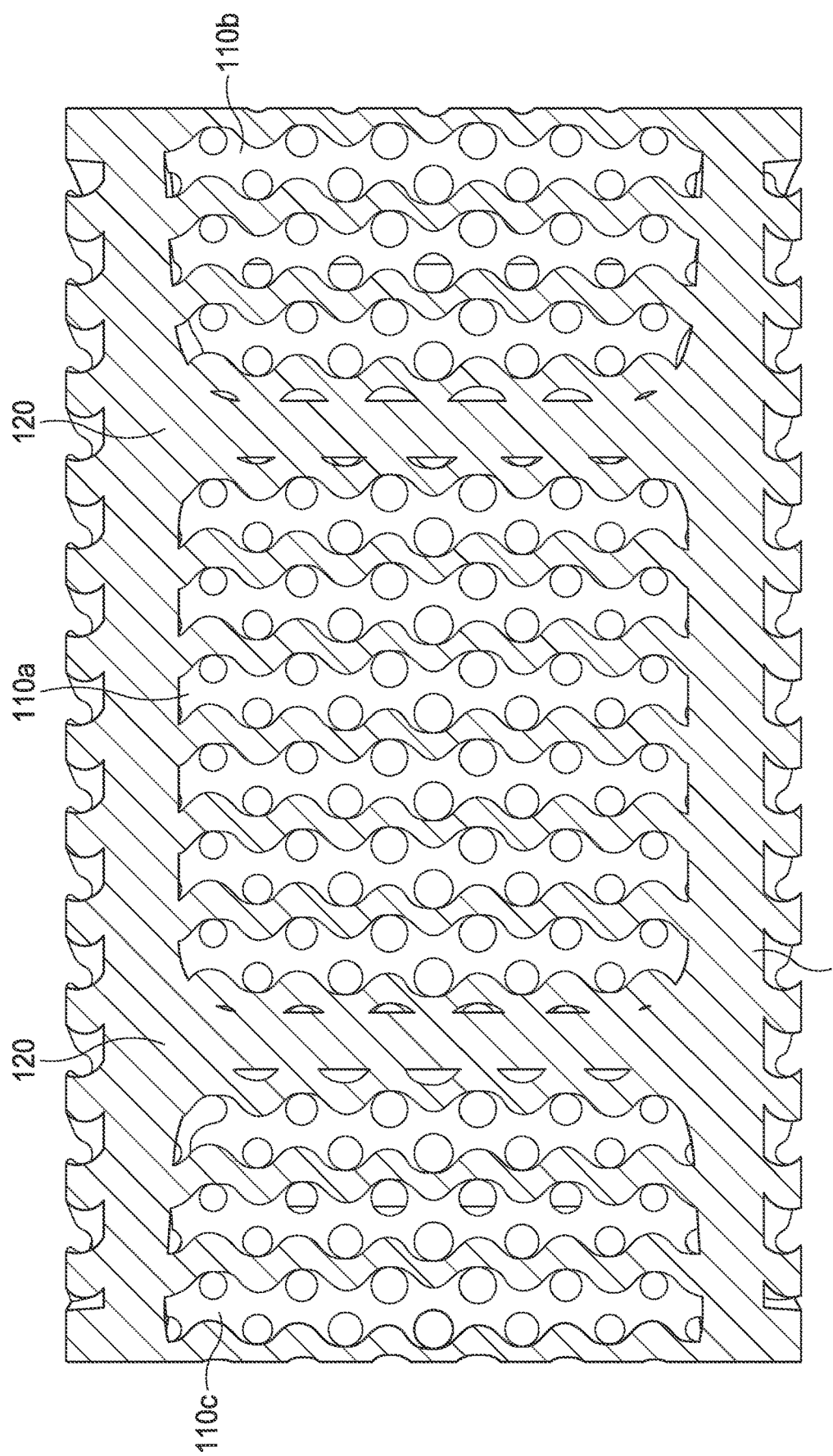
FIG. 4A is a cross-sectional view of the interbody implant of FIGS. 1A and 1B taken along line 4A-4A, according to aspects of the present disclosure.
Figure 4B:
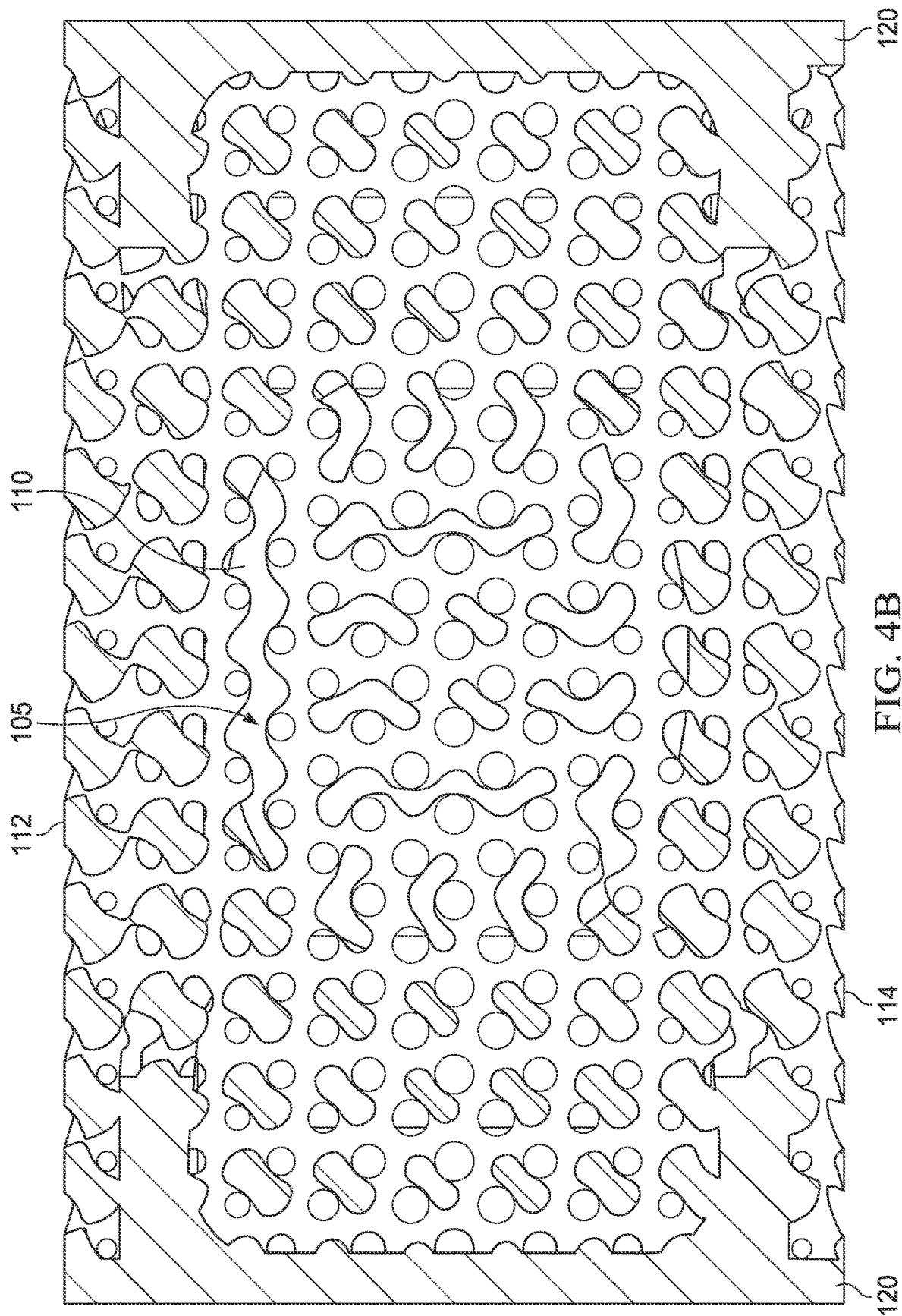
FIG. 4B is a cross-sectional view of the interbody implant of FIGS. 1A and 1B taken along line 4B-4B, according to aspects of the present disclosure.

FIGS. 4A, 4B, 4C, and 4D are cross-sectional views of the implant 100 shown in FIG. 1A taken along lines 4A-4A, 4B-4B, 4C-4C, and 4D-4D, respectively. FIGS. 4A and 4B are cross-sectional views of the implant 100 taken along parallel planes in the front side 102. The cross-section of FIG. 4A, which is taken along line 4A-4A, is closer to the outer surface of the first side 102. Accordingly, FIG. 4A shows the solid scaffold portions 120 separating the first visualization window 110a from the corner visualization windows 110b and 110c. By contrast, FIG. 4B is taken along a plane closer to the cavity 105 of the implant 100 such that the solid scaffold portions 120 separating the first visualization window 110a from the corner visualization windows 110b, 110c are not present. In this regard, it will be understood that the solid scaffold portions 120 extending vertically along the implant 100 are present in only a portion of the thickness of the first side 102. Accordingly, the porous structure of the implant 100 around the cavity 105 allows for increased bone in-growth and adhesion to the vertebrae.

FIG. 4B shows solid scaffold portions 120 at the left and right edges or corners of the implant 100. FIG. 4B also shows a portion of the central cavity 105. The porous structure of the implant 100 around the cavity 105 may form an interconnected network or lattice of passageways arranged in a periodic fashion, in which the passageways curve through the sidewalls of the implant 100 and intersect with one another.

Referring still to FIGS. 4A and 4B, the density or porosity gradient of the first side 102 is constant throughout the thickness of the first side 102. Accordingly, in the cross-sections of both FIG. 4A and FIG. 4B, the porosity increases toward the center of the visualization windows 110 and decreases toward the upper and lower portions of the visualization window 110. In some aspects, the upper and lower portions of the visualization window 110 may be referred to as outer portions or outer regions of the visualization window 110. The porosity may vary linearly or non-linearly. In the illustrated embodiment, the porosity varies in an ordered fashion according to a geometrical function describing a gyroid.

Figure 4C:
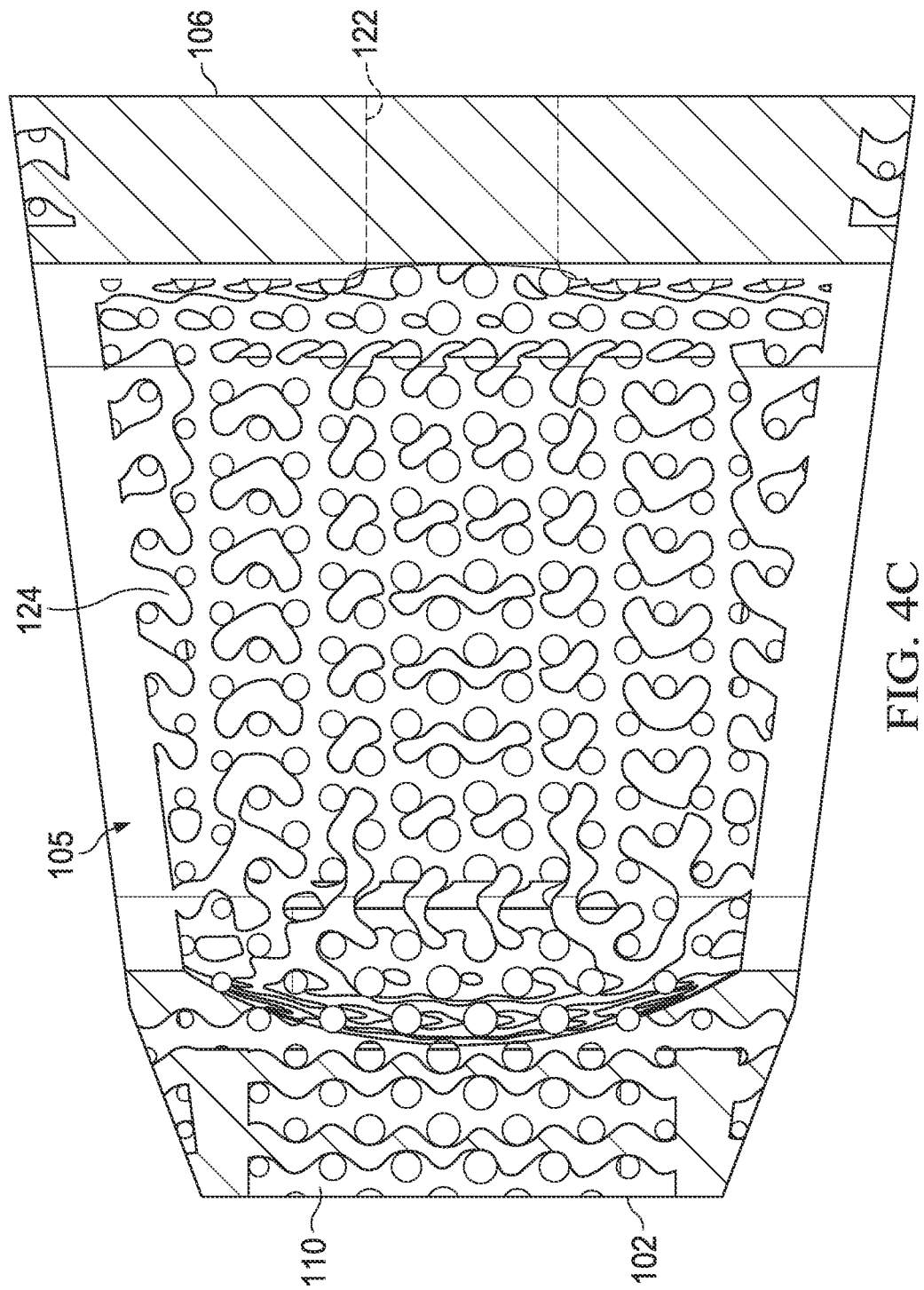
FIG. 4C is a cross-sectional view of the interbody implant of FIGS. 1A and 1B taken along line 4C-4C, according to aspects of the present disclosure.

FIG. 4C shows a cross-sectional view of the implant 100 taken along line 4C-4C, which extends from the front side 102 to the rear side 106 and through the cavity 105. The apertures or passageways of the visualization window 110 on the front side 102 extend through an entire thickness of the front side 102, and are in communication with the cavity 105. By contrast, the rear side 106 includes a solid portion extending through an entire thickness of the rear side 106.

Figure 4D:
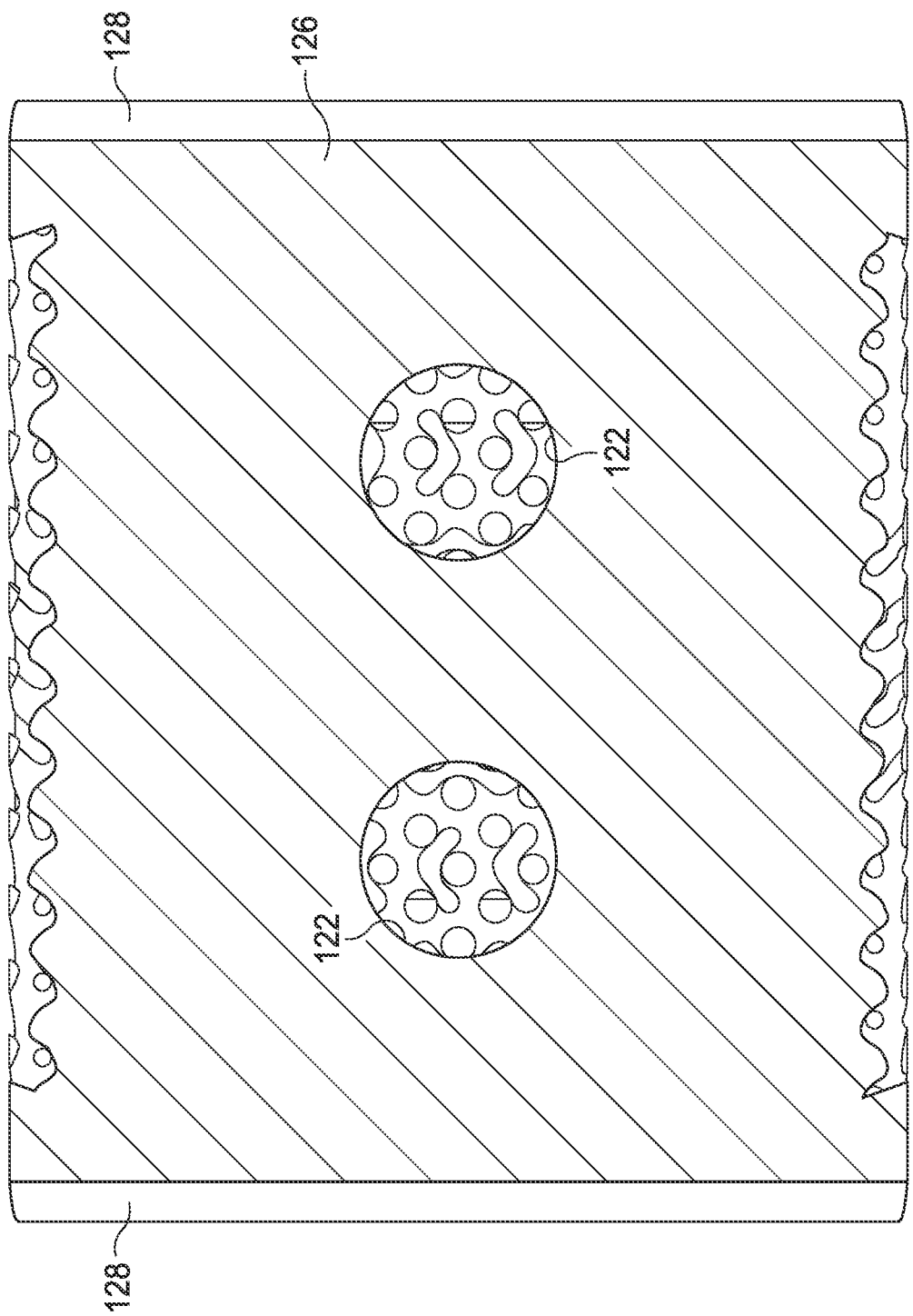
FIG. 4D is a cross-sectional view of the interbody implant of FIGS. 1A and 1B taken along line 4D-4D, according to aspects of the present disclosure.

FIG. 4D shows a cross-sectional view of the implant 100 taken along line 4D-4D, which extends through the rear side 106. The solid portion 126 is present throughout a thickness of the rear side 106 and surrounds or defines the positioning holes 122. The solid portion 126 extends around the corners 128 adjacent to the lateral sides 104, 108.

Figure 4E:
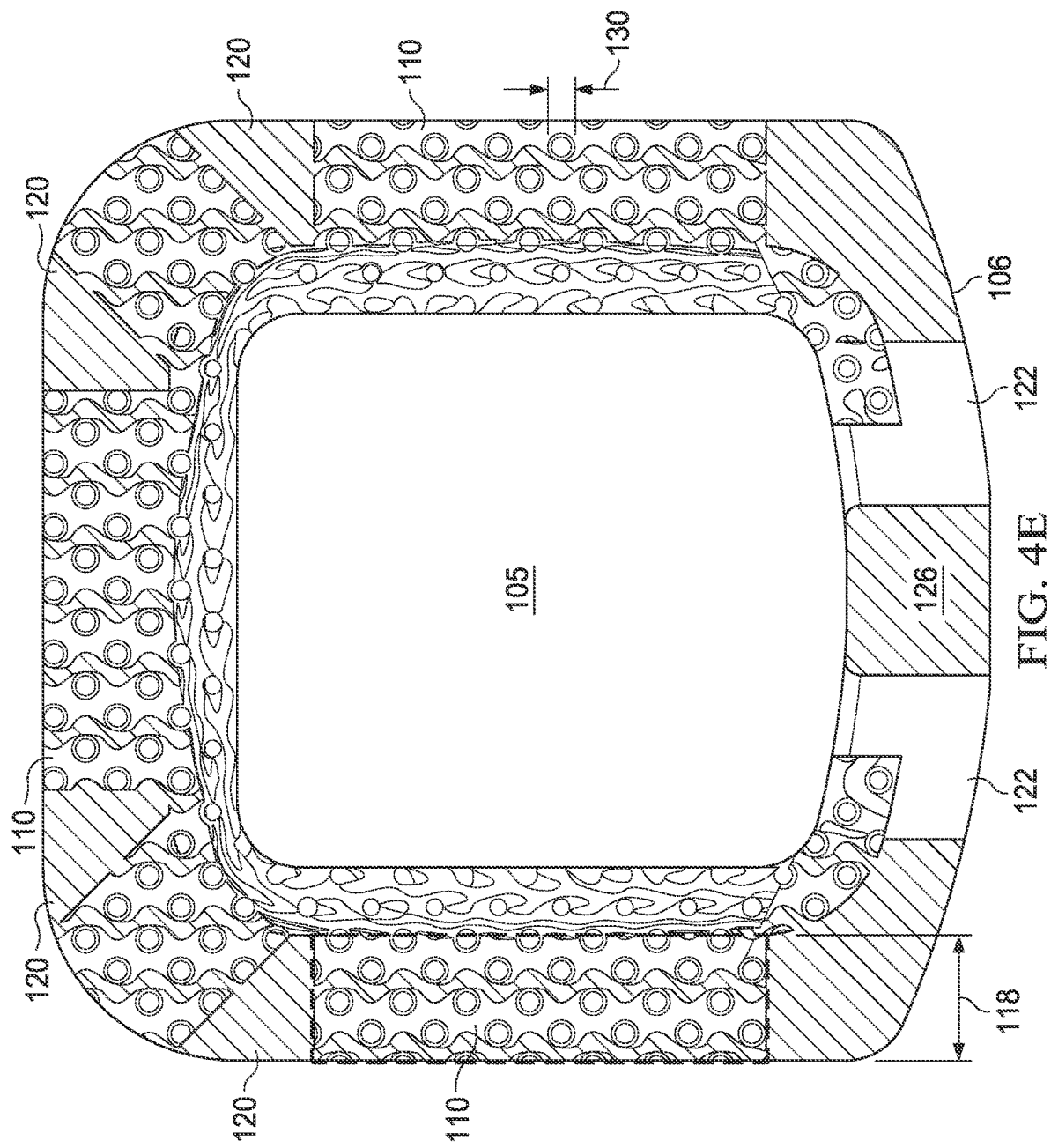
FIG. 4E is a cross-sectional view of the interbody implant of FIGS. 1A and 1B taken along line 4E-4E, according to aspects of the present disclosure.

FIG. 4E shows a cross-sectional view of the implant 100 taken along line 4E-4E. The cross-section shown in FIG. 4E shows a middle section of the implant 100, including the cavity 105. In some aspects, the cross-sectional view of FIG. 4E may be associated with a central region of the visualization windows 110 which have a heightened porosity and lower density. Because the cross-section of FIG. 4E is taken along a plane of constant height through the implant 100, the porosity may be constant across this plane. The solid scaffold portions 120 have wedge-shaped cross-sections such that the widest portions of the solid scaffold portions 120 are at the outer surfaces of the implant 100, and the solid scaffold portions 120 become increasingly narrow as they protrude inward toward the cavity 105. An interior surface of the implant 100 surrounding the cavity 105 may include an entirely or mostly apertured or porous surface. In the visualization windows 110 the apertures or passageways may be present in an entire thickness 118 of the implant 100.

Referring generally to FIGS. 1A-4E, one or more of the features of the implant 100 may be modified, adjusted, removed, or otherwise changed without departing from the scope of the present disclosure. For example, in some embodiments, one or more of the sides (102, 108) of the implant may include more than one visualization window 110 divided or defined by one or more additional solid scaffold portions 120. In some embodiments, the front side 102 and/or one of the lateral sides 104, 108 may not include a visualization window 110, and may be solid. In some embodiments, the front side 102 and/or one of the lateral sides 104, 108 may include a visualization having a constant porosity, such that only one of the visualization windows has a functional gradient for improved radiotransparency. In some embodiments, the rounded corners of the implant 100 are solid, and do not include visualization windows 110. In some embodiments, at least a portion of the rear side 106 includes a porous portion, and may include a visualization window 110. In some embodiments, the porosity of the visualization windows 110 varies through the thickness of the sidewall toward the cavity 105. For example, the porosity may increase from an exterior surface of the implant 100 to an interior surface of the implant 100, wherein the interior surface surrounds and defines the cavity 105.

Figure 5:
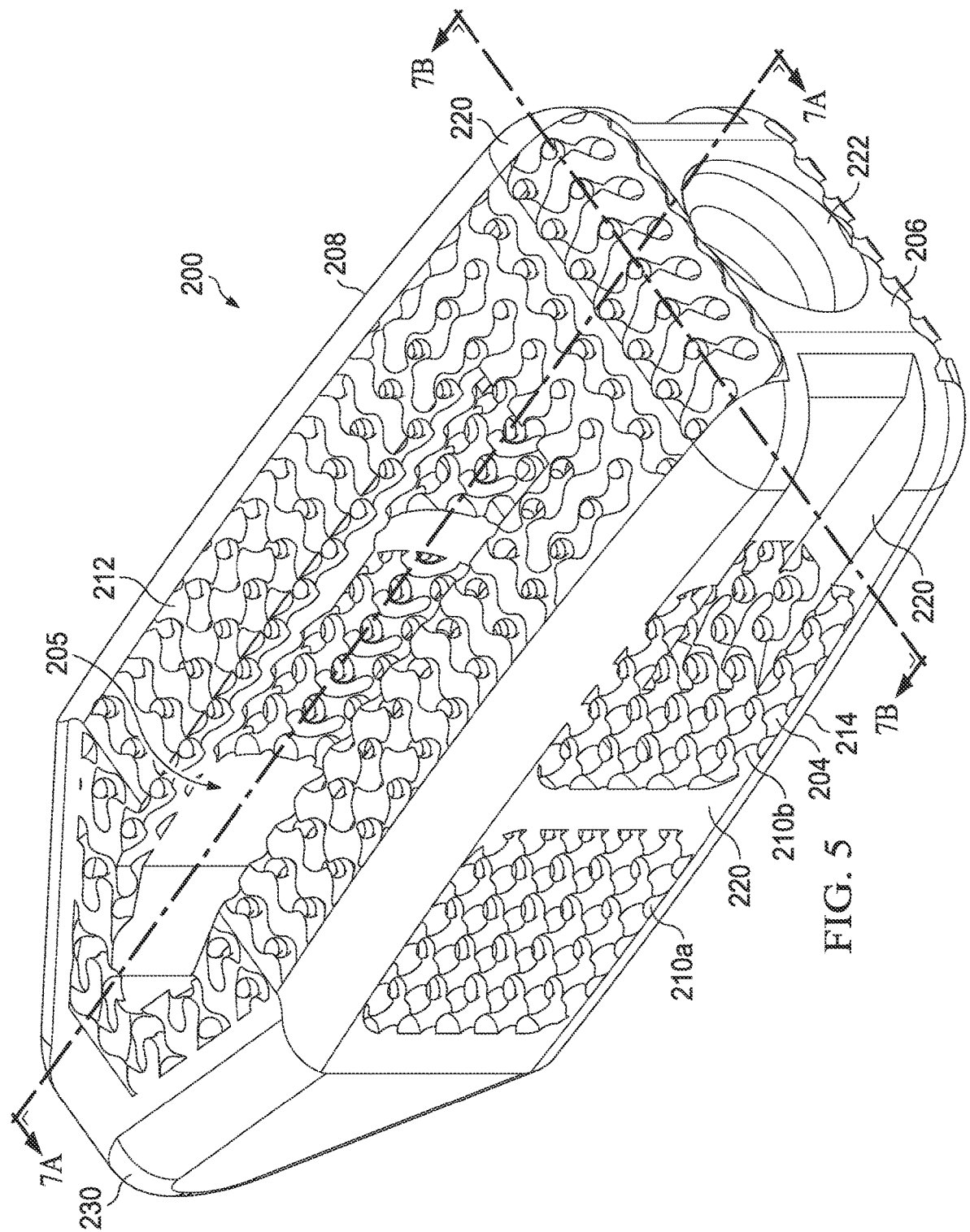
FIG. 5 is a perspective view of a lumbar interbody implant having a plurality of visualization windows according to aspects of the present disclosure.
Figure 6:
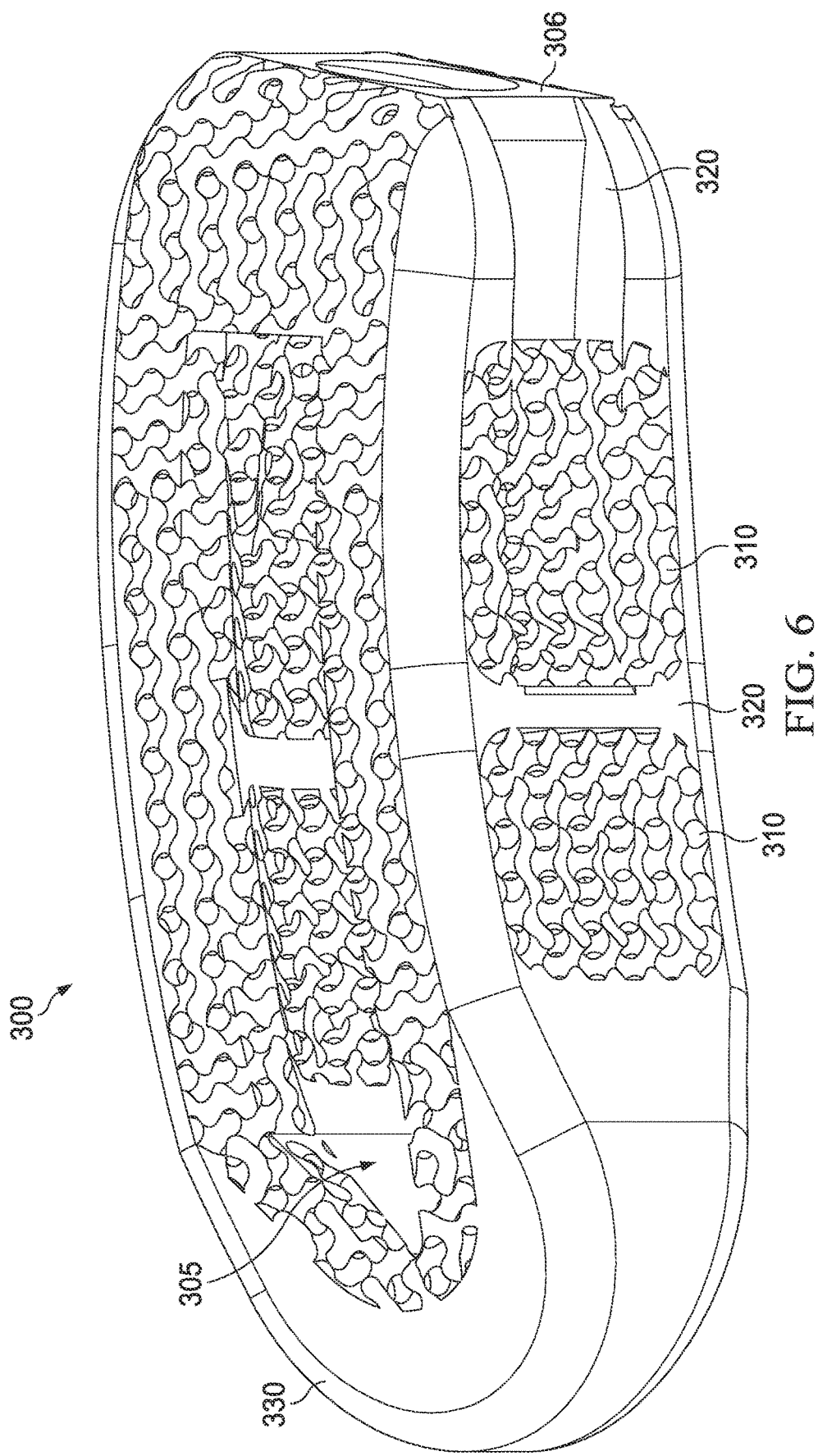
FIG. 6 is a perspective view of a lumbar interbody implant having a plurality of visualization windows according to aspects of the present disclosure.

FIGS. 5 and 6 are perspective views of lumbar interbody implants 200, 300, according to aspects of the present disclosure. Referring to the implant 200 shown in FIG. 5, the implant 200 includes a plurality of visualization windows 210 and a plurality of scaffold portions 220, similar to the implant 100 shown in FIGS. 1A-4E. The implant 200 includes a plurality of lateral sides or surfaces, including a lateral side 204, a rear side 206 and a lateral side 208, each arranged around a cavity 205. The implant 200 includes apertured portions and solid portions. The apertured portions may be referred to as porous portions, where the pores include a network of holes or passages in the body of the implant 200. The apertured portions may also be referred to as cavernous portions, cavitated portions, for example. The implant 200 also includes a nose portion 230 including one or more solid surfaces having an angled or conical shape. The visualization windows 210 and the solid scaffold portions 220 and the nose portion 230 define and surround a cavity or opening 205. The opening 205 may extend from a top surface 212 to a bottom surface 214. In some embodiments, the opening 205 extends from the top surface 212 to an intermediate portion such that the opening 205 does not extend through an entire height of the implant 200. Similar to the implant 100 shown in FIGS. 1A and 1B, the rear side 206 of the implant 200 includes a positioning hole 222. The positioning hole 222 is configured to receive a positioning tool for placement of the implant 200 and between the vertebrae of the patient's spine. The rear side 206 comprises a solid surface surrounding and defining the positioning hole 222. The solid surface or portion of the rear side 206 may extend an entire thickness of the rear side 206, or a portion of the thickness of the rear side 206.

Referring still to FIG. 5, a solid scaffold portion 220 is disposed in a central region of the lateral side 204 between two visualization windows 210a, 210b. An identical or similar scaffold portion 220 may be present on the lateral side 208. In some aspects, the additional solid scaffold portions 220 shown in the embodiment of FIG. 5 provide additional support and strength for the implant 200, which is longer than the implant 100 shown in FIGS. 1A and 1B. Further, it will be understood that the implant 200 shown in FIG. 5 may experience larger forces than the implant 100 shown in FIGS. 1A and 1B, since the implant 200 is used in between the lumbar vertebrae and not the cervical vertebrae. The visualization windows 210 have varying densities along at least one direction or axis. In this regard, the visualization windows 210 have a density gradient or porosity gradient along a height of the implant 200 such that density is the lowest at a middle height of the implant 200.

The nose portion 230 facilitates insertion of the implant 200 between the lumbar vertebrae. For example, when advancing the nose portion 230 of the implant 200 in a space between adjacent vertebrae of the spine, the vertebrae may separate to provide space for the implant 200. Similar to the implant 100 shown in FIGS. 1A and 1B, the implant 200 may include a wedge shape such that the rear side 206 is smaller or shorter in the direction compared to the height at the base of the nose portion 230. Accordingly, the implant includes an inclined or wedged shape profile configured to conform to the curvature of the spine (lordosis). In some aspects the implant 200 may be used in a pair such that two implants 200 are positioned next to each other between the lumbar vertebrae.

Referring to FIG. 6, and implant 300 includes a nose portion 330 visualization windows 310 solid scaffold portions 320 a rear side 306 lateral sides 304, 308, each arranged around a cavity 305. The implant 300 includes apertured portions and solid portions. In some aspects, the apertured portions may be referred to as porous portions, where the pores include a network of holes or passages in the body of the implant 300. The apertured portions may also be referred to as cavernous portions, cavitated portions, for example. The implant 300 has a curved shape for use in the lumbar vertebrae in a different configuration than the implant 200. For example, the implant 300 may be inserted between the lumbar vertebrae in a sideways direction (e.g., transpsoas approach). In another example, the implant 300 may included in a pair of similar implants which extend in parallel between adjacent vertebrae in the spine. In some aspects, the size of the lateral side 308 may be different from the size of the lateral side 304, to account for the curvature of the spine.

Figure 7A:
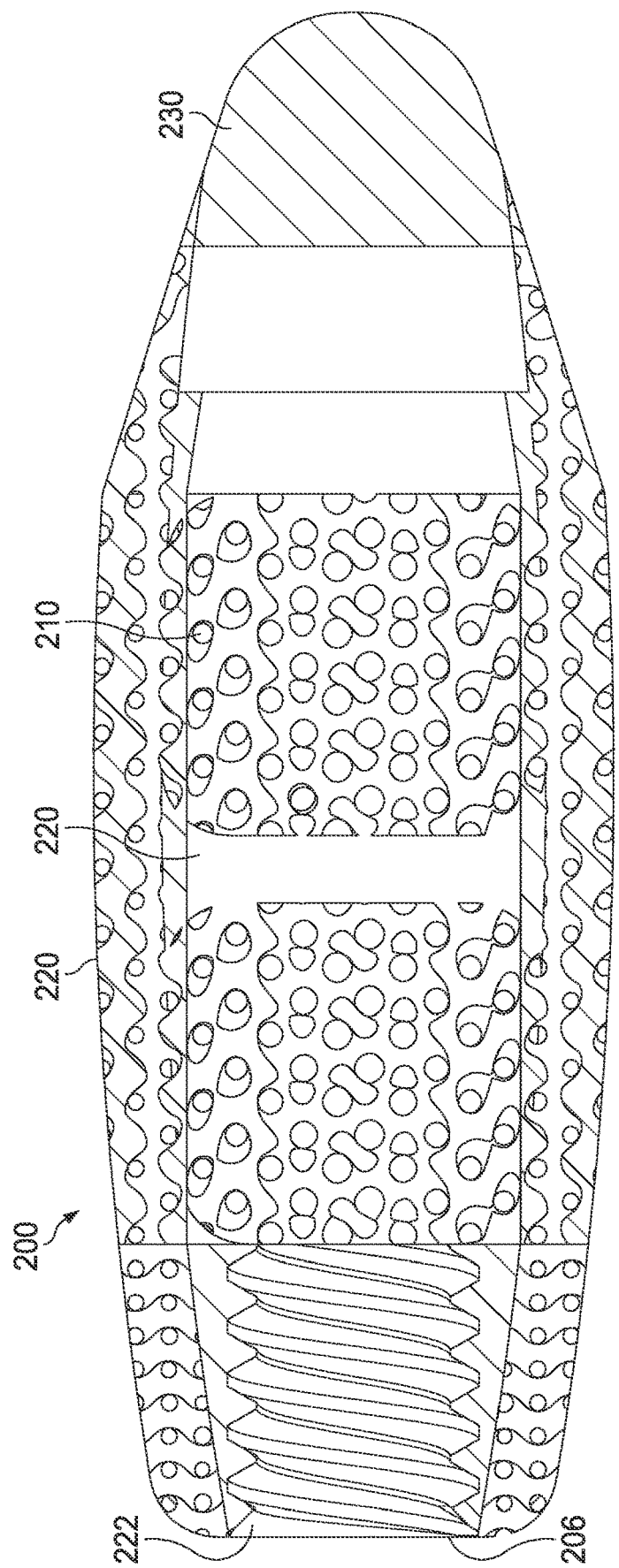
FIG. 7A is a cross-sectional view of the interbody implant shown in FIG. 5 taken along line 7A-7A, according to aspects of the present disclosure.
Figure 7B:
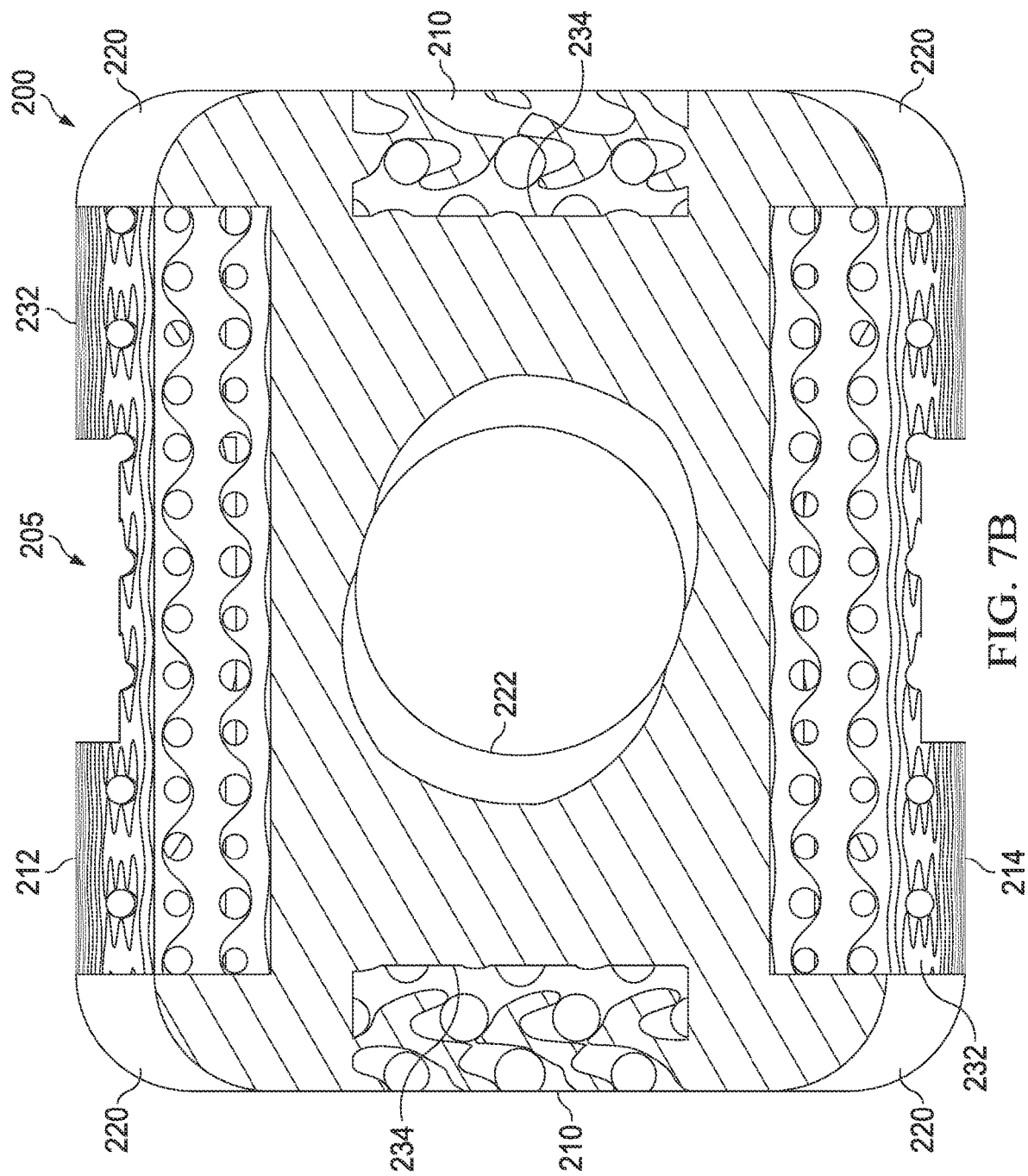
FIG. 7B is a cross-sectional view of the interbody implant shown in FIG. 5 taken along line 7B-7B, according to aspects of the present disclosure.

FIGS. 7A and 7B are cross-sectional views of the implant 200 shown in FIG. 5 taken along the lines 7A-7A and 7B-7B, respectively. Referring to FIG. 7A, the implant 200 includes solid scaffold portions 220, visualization windows 210, and a solid nose portion 230. The solid scaffold portions 220 form a structural frame for the implant 200 to provide strength and resist deformation under pressure in the spine. The solid nose portion 230 may be rigid and durable to facilitate positioning of the implant 200 between vertebrae. In this regard, the nose portion 230 of the implant 200 may be inserted between adjacent vertebrae, and pushed or tapped into place using a positioning tool coupled to the implant by the positioning hole 222. In the illustrated embodiment, the positioning hole 222 is threaded and configured to couple to a corresponding threaded positioning tool.

The visualization windows 210 are shown on one side of the implant 200, with a vertically-extending scaffold portion 220 positioned between the visualization windows 210. The visualization windows 210 are at least partially radiolucent or radiotransparent such that the cavity of the implant 200 can be monitored and inspected using x-ray imaging. In one aspect, the cavity of the implant is filled with bone growth promoting material and the visualization window permits radiograph inspection of the progress of bone growth over a period of time after implantation, such as days, weeks, months or years. The visualization windows 210 have a gradient of porosity or radiotransparency that increases toward a center of the visualization windows 210 along at least a vertical direction from the top surface 212 to the bottom surface 214, which may be referred to as the vertical axis. In some embodiments, the gradient of porosity or radiotransparency of the visualization windows 210 also varies along the horizontal axis. The visualization windows 210 may include constant porosity or constant radiotransparency regions near the top and/or bottom of the visualization windows 210, in some embodiments.

FIG. 7B is a cross sectional view of the implant 200 taken along line 7B-7B, which shows a largely solid region of the body of the implant 200 at the rear solid scaffold portion 220 near the positioning hole 222. The solid scaffold portion 220 extends around the corners of the implant 200, and porous portions 232 are present on a top side and a bottom side of the implant 200. The lateral sides include recesses 234, and the exterior surfaces of the visualization windows 210 can be seen beyond the recesses 234. The cavity 205 extends through the implant 200 from the top surface 212 to the bottom surface 214. The porous portions 232 have a lower porosity than the visualization windows 210, which are closer to a center of the implant with respect to the vertical axis. Accordingly, the porous portions 232 may allow for bone growth into the porous structure, but provide less radiotransparency than the visualization windows 210.

Although the implants 200 and 300 shown in FIGS. 5-7B have different shapes, sizes, and structural configurations than the implant 100 shown in FIGS. 1A-4E, each of the implants 100, 200, 300 allow for radiological imaging through the visualization windows 110, 210, 310 through at least one side of the implant, while maintaining sufficient strength to support the load applied to each device when implanted in the spine. The implants 100, 200, 300 each have reinforcing structures, referred to in some embodiments as scaffolding portions, to provide strength and rigidity around the edges or perimeters of the visualization windows 110, 210, 310, which are radiotransparent in at least a central region to allow for monitoring of bone in-growth in the cavities of each implant. The scaffolding portions provide a skeleton, with the visualization windows occupying the space between portions of the skeleton. The particular gradient used for each type of implant, the size of the scaffolding portions, the overall dimensions of the implant, the thickness of the sidewalls, and other geometric and structural parameters may be selected based on the application of the implant (e.g., lumbar, cervical, etc.).

Figure 8A:
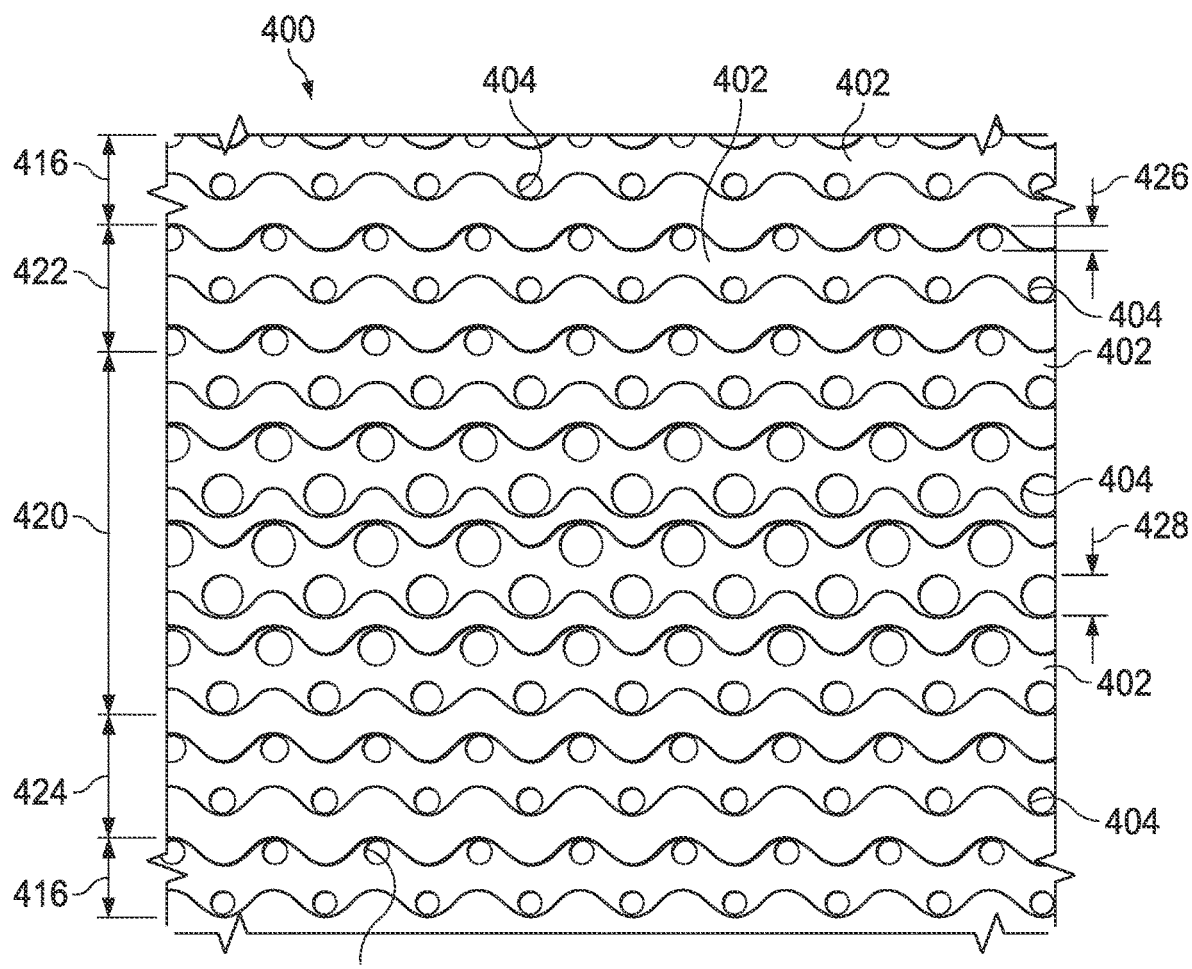
FIG. 8A is an elevation view of a density or porosity gradient of a visualization window of an interbody implant according to aspects of the present disclosure.
Figure 8B:
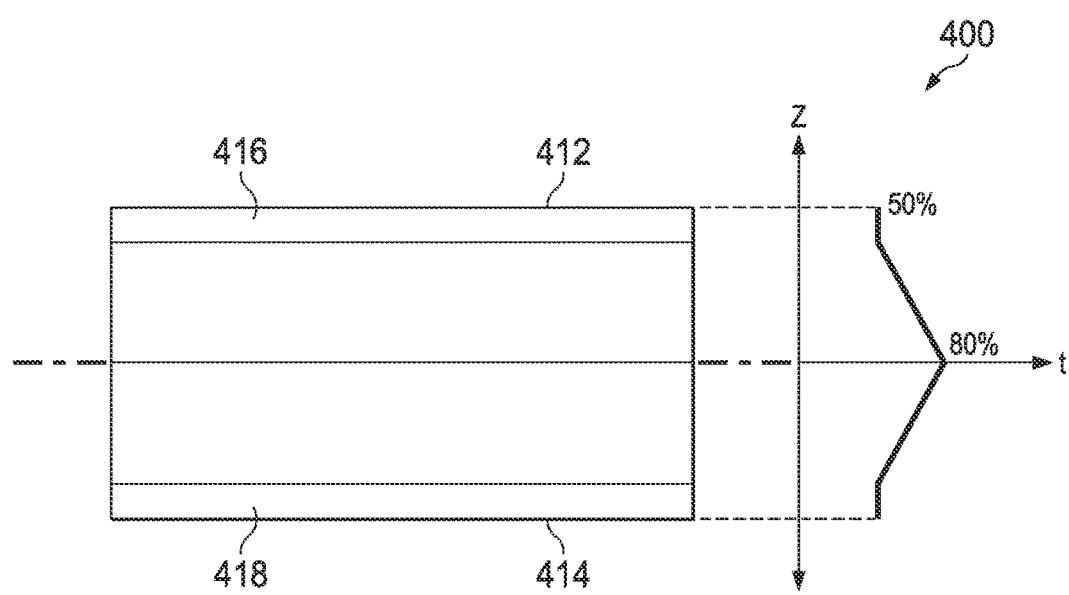
FIG. 8B is a graphical view of a density or porosity gradient of a visualization window of an interbody implant according to aspects of the present disclosure.

FIGS. 8A and 8B illustrate the gradient or density profile of a visualization window 400, according to some embodiments of the present disclosure. The visualization window 400 may be one of the visualization windows 110, 210, or 310, or may otherwise be applied to the implants 100, 200, and/or 300. FIG. 8A is an elevation view of a density or porosity gradient of a visualization window 400 of an interbody implant. FIG. 8B is a graphical view of the density or porosity gradient of the visualization window. As similarly described above, the visualization window 400 includes a lattice or network of structures defining channels, tunnels, or pores in a sidewall of the implant. On the surface shown in the illustrated embodiment, the porosity or density is associated with a size (e.g., diameter) of the openings or apertures 404, which are periodically arranged across the visualization window 400, with each row of apertures offset from a neighboring row by half the distance between neighboring apertures in a given row. Stated differently, the density is associated with a proportion of solid portions 402 to the apertures 404. The lattice or network of solid structures, surfaces, and apertures forms a gyroid structure, such that the apertures 404 are interconnected. The visualization window 400 varies in porosity along a vertical axis.

The visualization window 400 includes constant density regions 416 at the top and bottom portions of the visualization window 400, which extend from the top surface 412 and bottom surface 414. In the constant density regions 416, the size of the apertures 404 does not increase or decrease. Accordingly the density of the constant density regions 416 is relatively high. For example, referring to FIG. 8B, the density of the constant density regions 416 is approximately 50%, and is constant or flat throughout the constant density regions 416.

The visualization window 400 also includes outer regions 422, 424, and a central region 420. In FIG. 8A, the outer regions 422, 424, and central region 420 may be defined arbitrarily based on the density of the lattice at various locations along the vertical axis of the window 400. In this regard, in the embodiment of FIGS. 8A and 8B, the porosity varies linearly from outer boundaries of the outer regions 422, 424 to a center of the central region 420. The porosity reaches a maximum of 80% at the center of the central region 420. Thus, the outer regions 422, 424 may be defined as having relatively lower porosity closer to 50%, and the central region may be defined as having relatively higher porosity closer to 80%. Accordingly, the central region 420 is more radiotransparent than the outer regions 422, 424. In some embodiments, the central region 420 may be sufficiently radiotransparent to allow for x-ray imaging through an entire thickness of the visualization window 400 into an interior cavity of the implant. In some embodiments, the central region 420 may be sufficiently radiotransparent to allow x-ray imaging of material beyond the central cavity, and even outside of the implant on an opposing side. For example, the central region 420 may be sufficiently radiotransparent to allow x-ray imaging of material within an opposing sidewall and/or an opposing visualization window on the other side of the device.

The porosity, as a percentage, may be determined by dividing porous volume with the overall volume. In some aspects, the porosity is inversely related with the lattice density. For example the porosity may be inversely proportional to lattice density. When using an ordered porous structure as shown in FIG. 8A, the porosity may be based on or otherwise associated with the diameter of the apertures 404 at a given vertical position. For example, at the center of the visualization window 400 with a porosity of 80%, the diameter of the apertures 404 at this location may range from 550 µm to 750 µm. In the constant density regions with a porosity of 50%, the diameter of the apertures may range from 150 µm to 550 µm. In some embodiments, the porosity may be controlled or modified based on a spacing of the apertures 404 in the lattice structure. Further, it will be understood that the 50% and 80% porosity values are exemplary, and do not limit the scope of the present disclosure. For example, in some embodiments, the porosity of the constant density regions may be between 30% and 55%. In some embodiments, the maximum porosity at the central region 420 of the visualization window 400 may be between 70% and 90%.

The porosity of the visualization window 400 at a given position along the vertical axis is based on the size of the apertures 404. The size of the apertures 404, and therefore the porosity, linearly increases in the outer regions 422, 424 and the central region 420 as the distance from the center of the central region 420 decreases. For example, a diameter 426 of an aperture 404 at a first position in the outer region 422 is smaller than a diameter 428 of an aperture 404 near the center of the central region 420. Described in another, the proportion of the solid portions 402 to apertures 404 decreases from the outer regions 422, 424 to the center of the central region 420.

The size of the apertures may vary linearly in the lattice or network of the window 400 based on a function defining a shape of the lattice structure. For example, the size of the apertures 404 at a given vertical position may be determined or based on one or more coefficients of a gyroid equation used to determine the shape of the lattice structure. In other embodiments, the porosity may be based on a spacing of the apertures 404 from the neighboring apertures, and/or a number of apertures 404 for each unit of surface area or volume (e.g., $cm^2$, $cm^3$).

In some embodiments, the porosity or density of the visualization window 400 varies along the horizontal axis in addition to the vertical axis. For example, in some embodiments, the visualization window 400 includes lateral outer regions having a lower porosity than the central region. The density may vary linearly or non-linearly along the horizontal axis. The density may also vary though a thickness of the visualization window 400, in some embodiments. Further, in some embodiments, the visualizations windows described herein may comprise rectangular or non-rectangular shapes, including circular shapes, elliptical shapes, hexagonal shapes or any other suitable shape. The arrangement of the apertures 404 or pores may be ordered or random. In other embodiments, the density gradient may be non-linear. For example, the density gradient may follow a gaussian curve, a quadratic curve, a linear stepped function, or any other suitable type of profile.

Figure 9:
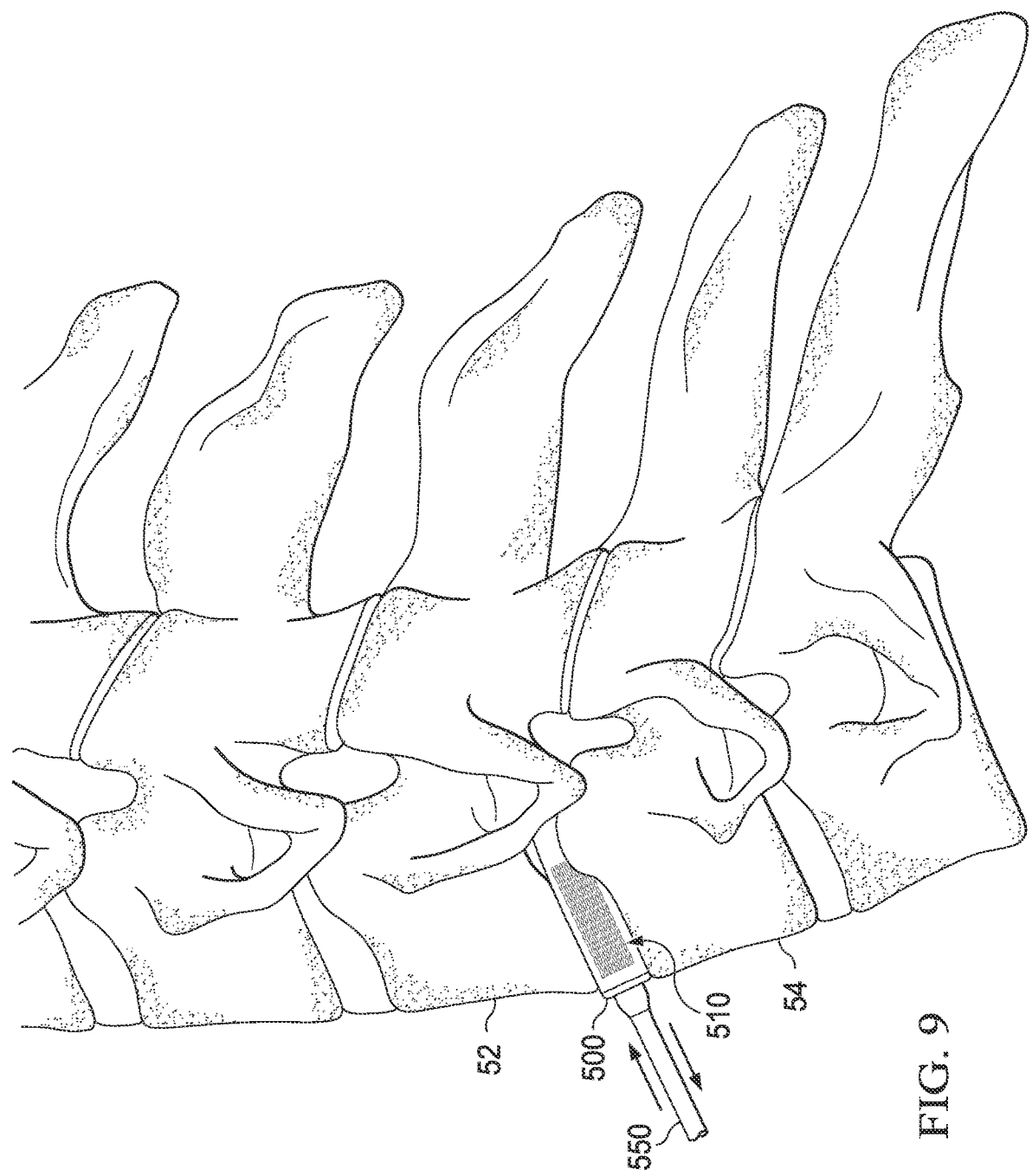
FIG. 9 is a perspective view of an interbody implant having a visualization window being positioned between adjacent vertebrae of a patient's spine during a spinal fusion surgical procedure, according to aspects of the present disclosure.

FIG. 9 is a perspective view of an interbody implant 500 having a visualization window 510 being positioned between adjacent vertebrae 52, 54 of a patient's spine, according to aspects of the present disclosure. The implant 500 is positioned using an insertion tool 550. The insertion tool may be coupled to the device via one or more positioning holes (e.g., 122, FIG. 3B) on a side of the implant 500. The visualization window 510 is positioned on a lateral side of the implant 500, such that an interior of the implant 500 may be viewed through the visualization window 510 by obtaining an x-ray image along a coronal plane of the patient. For example, the implant 500 may include an internal cavity or opening. The implant 500 is configured to bind with the vertebrae 52, 54 using a bone graft material. The bone in-growth within the cavity of the implant 500 may be observed by obtaining x-ray images through the visualization window. The radiotransparency of at least a portion of the visualization window 510 may be sufficient to allow for monitoring the bone in-growth in the cavity, and within the cavernous structure of the visualization window.

Figure 10:
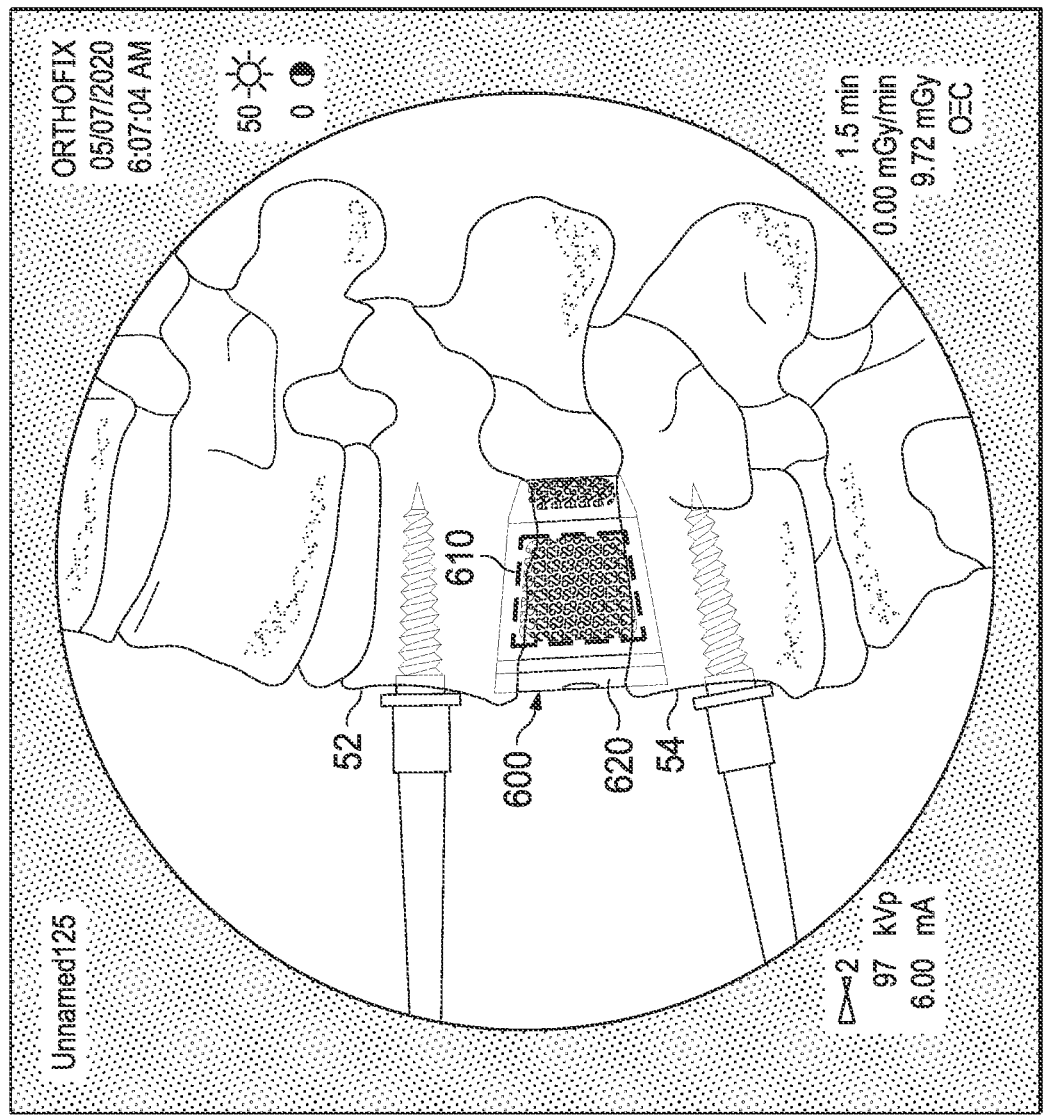
FIG. 10 is a representation of a radiological image showing an interbody implant having a visualization window being positioned between adjacent vertebrae of a patient's spine, according to aspects of the present disclosure.

FIG. 10 is a representation of a radiological image of an interbody implant 600 having a visualization window 610 and being positioned between adjacent vertebrae 52, 54 of a patient's spine, according to aspects of the present disclosure. The visualization window 610 includes a functional gradient in which a porosity or density increases along at least one axis, according to an embodiment of the present disclosure. The implant 600 further includes one or more solid scaffold portions 620 around a perimeter of the lateral sides of the implant 600. The scaffold portions 620 provide for added strength to allow the implant 600 to retain its shape, even with relatively lower density and porous portions in the visualization window 610.

As mentioned above, with the implant 600 in place, the visualization window 610 allows the physician to observe the progress of bone in-growth in the implant 600. Further, the scaffold portions 620 and the functional gradient of the visualization window 610 allow for enhanced radiotransparency while maintaining structural strength and integrity under the force of the spine.

As mentioned above, the implants described herein (e.g., 100, 200, 300, 500, 600) may be manufactured using an additive manufacturing process. For example, the implants may be formed by a 3D printing process, or by a metal sintering process. In some embodiments, an implant is formed by depositing a layer of metallic (and/or polymer) power on a substrate, and laser sintering the portions of the layer that will be incorporated into the device. The geometry of the layers may be determined based on a pre-defined porous geometric structure (e.g., gyroid), where individual slices of the geometric and extracted and rendered according to the operating parameters of the metal sintering device. This process can be repeated layer-by-layer until the implant is formed. The un-sintered power can be removed from the structure, leaving a unitary or monolithic implant which has a functional gradient including the lattice structures described herein.

According to one embodiment, an implant may be formed by depositing or sintering a plurality of regions having different densities or density ranges. For example, a first region having a first density or first density range may be deposited, printed, sintered, or otherwise formed. The first region may include a lattice structure having a network of interconnected passageways or pores having a first pore size. For example, the first region may correspond to the constant density regions 416 shown in FIGS. 8A and 8B. Accordingly, in some embodiments, the first region comprises a first lattice density along at least one axis, and in particular, a vertical axis.

In a following step, a second region having a second density or second density range may be deposited, printed, sintered, or otherwise formed on top of the first region. The second density or second density range may have a lower density than the first region. For example, the second region may correspond to the outer region 424 shown in FIG. 8A. Accordingly, the second region may have a gradient of lattice density that varies along at least the vertical axis.

In a following step, a third region having a third density or third density region may be deposited, printed, sintered, or otherwise formed on top of the second region. The third density or third density range may have a lower density than the second region. For example, the third region may correspond to the central region 420 shown in FIG. 8A. Accordingly, the third region may have a gradient of lattice density that varies along at least the vertical axis. In particular, the third region may vary such that the density reaches a minimum at or near a center of the third region along the vertical axis.

In some embodiments, the method for manufacturing the implant further includes depositing a fourth region and a fifth region on top of the third region. For example, the fourth region may correspond to the outer region 422, and the fifth region may correspond to the upper constant density region 416 shown in FIG. 8A. Accordingly, the density profile of the implant may be symmetrical about a horizontal plane extending through the center of the implant.

In some embodiments, depositing each of the first, second, and third regions includes depositing a plurality of layers that vary incrementally according to a geometric function, such as a gyroid function. The parameters of the gyroid function may determine the pore size of the lattice structure, and therefore the lattice density, at each individual layer or slice.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An interbody device configured for insertion between adjacent vertebrae, the interbody device comprising:
   a body comprising an exterior surface and an interior surface defining a cavity, wherein the body comprises a visualization window extending between the exterior surface and the interior surface, wherein the visualization window comprises a lattice of radiopaque structures,
   wherein a density of the lattice in a central region of the visualization window is less than a density of the lattice in an outer region of the visualization window such that the visualization window is radiolucent through the central region.

2. The interbody device of claim 1, wherein the body comprises a top side and a bottom side, and wherein the lattice comprises a first density gradient along a first direction extending between the top side and the bottom side.

3. The interbody device of claim 2, wherein the lattice comprises a second density gradient along a second direction transverse to the first direction.

4. The interbody device of claim 2, wherein the first density gradient linearly decreases from the outer region of the visualization window to the central region of the visualization window.

5. The interbody device of claim 1, wherein the density of the lattice of the outer region of the visualization window is associated with a porosity of 40%-60%, and wherein the density of the lattice of the central region of the visualization window is associated with a porosity of 70%-90%.

6. The interbody device of claim 1, wherein the visualization window comprises a first constant density region in the outer region.

7. The interbody device of claim 6, wherein the first constant density region extends from a bottom edge of the body to a first intermediate region between the bottom edge and the central region of the visualization window.

8. The interbody device of claim 1, wherein the lattice of radiopaque structures comprises a gyroid architecture.

9. The interbody device of claim 8, wherein at least one of the density of the lattice in the central region or the density of the lattice in the outer region is based on geometric parameters of the gyroid architecture.

10. The interbody device of claim 1, wherein the body comprises a plurality of solid scaffold regions, wherein the visualization window is disposed between two solid scaffold regions.

11. The interbody device of claim 10, wherein the body comprises a sidewall extending from the exterior surface to the interior surface, and wherein the plurality of solid scaffold regions occupy only a portion of a thickness of the sidewall.

12. The interbody device of claim 1, further comprising a solid wall on a lateral side of the body, wherein the body defines one or more passages extending through the solid wall on the lateral side of the body.

13. The interbody device of claim 1, wherein the body comprises a sidewall extending from the exterior surface to the interior surface, and wherein the lattice of the visualization window occupies an entire thickness of the sidewall.

14. The interbody device of claim 1, wherein the lattice of radiopaque structures comprises a metal.

15. The interbody device of claim 14, wherein the lattice of radiopaque structures comprises titanium.

16. An intervertebral spacer configured to be placed between two adjacent vertebrae, the intervertebral spacer comprising:
    a solid portion comprising a plurality of solid scaffold regions, wherein the solid scaffold regions are disposed around an opening; and
    a visualization window disposed between two or more of the solid scaffold regions and around the opening,
    wherein the visualization window comprises a lattice of radiopaque surfaces defining a network of pores,
    wherein a density of the lattice is greater in an outer region of the visualization window than in a central region of the visualization window such that the visualization window is radiolucent in the central region.

17. The intervertebral spacer of claim 16, wherein the solid portion and the visualization window form a unitary body.

18. The intervertebral spacer of claim 16, wherein the lattice varies linearly in density from the outer region to a center of the central region along a vertical axis.

19. The intervertebral spacer of claim 16, wherein the visualization window further comprises a constant density region positioned above the outer region such that the outer region is disposed between the constant density region and the central region, wherein the density of the lattice is constant in the constant density region along a vertical axis.

20. The intervertebral spacer of claim 16, wherein the network of pores extends from an exterior surface to the opening.

* * * * *